US006556951B1

(12) United States Patent
Deleo et al.

(10) Patent No.: US 6,556,951 B1
(45) Date of Patent: Apr. 29, 2003

(54) SYSTEM AND METHOD FOR INTELLIGENT QUALITY CONTROL OF A PROCESS

(75) Inventors: James M. Deleo, Bethesda, MD (US); Alan T. Remaley, Bethesda, MD (US)

(73) Assignee: The United States of America as represented by the Secretary of the Department of Health and Human Services, Washington, DC (US)

(*) Notice: Subject to any disclaimer, the term of this patent is extended or adjusted under 35 U.S.C. 154(b) by 0 days.

(21) Appl. No.: 09/555,325

(22) PCT Filed: Nov. 24, 1998

(86) PCT No.: PCT/US98/25182

§ 371 (c)(1),
(2), (4) Date: Jun. 16, 2000

(87) PCT Pub. No.: WO99/27466

PCT Pub. Date: Jun. 3, 1999

Related U.S. Application Data

(60) Provisional application No. 60/066,624, filed on Nov. 26, 1997.

(51) Int. Cl.[7] .............................................. G06F 15/00
(52) U.S. Cl. ........................ 702/183; 702/182; 702/186; 706/15
(58) Field of Search .................................. 702/183, 185, 702/182, 186, 187, 188; 700/48–50; 706/15, 21, 45

(56) References Cited

U.S. PATENT DOCUMENTS

| 5,016,188 A | 5/1991 | Lan |
| 5,041,976 A | 8/1991 | Marko et al. |
| 5,159,660 A | 10/1992 | Lu et al. |
| 5,282,261 A | 1/1994 | Skeirik |
| 5,565,364 A | * 10/1996 | Schaefer et al. ............. 436/161 |
| 5,687,716 A | * 11/1997 | Kaufmann et al. .......... 600/300 |
| 5,819,226 A | * 10/1998 | Gopinathan et al. ........... 705/44 |

FOREIGN PATENT DOCUMENTS

| EP | 0712605 A1 | 9/1995 |
| EP | 0 712 605 | 5/1996 |

OTHER PUBLICATIONS

Hwarng et al. ("Back Propagation Pattern Recognizers for X Control Charts: Methodology and Performance", Computers ind. Engng vol. 24, No. 2, pp. 219–235; 1993).*
Zatari et al., "In vivo liver differentiation by ultrasound using an artificial neural network," *Journal of the Acoustical Society of America*, vol. 96, No. 1, pp. 376–381 (Jul. 1994).

(List continued on next page.)

*Primary Examiner*—Bryan Bui
(74) *Attorney, Agent, or Firm*—Klarquist Sparkman, LLP

(57) ABSTRACT

A method and system for detecting errors in a process such as laboratory analysis of patient specimens and generation of test results is described. The steps of the method include collecting data elements having a range of values from the process. The number of data elements having values within predetermined intervals of the range are then counted. The counts of the data elements are applied as inputs to nodes of a neural network, each count being applied to a node representing the predetermined interval corresponding to the count. Output is then generated from the neural network based on the inputs, the output indicative of whether an error in the process (such as bias error or a precision error) has occurred. If the technology is used with a laboratory instrument, the output is generated in real time and available immediately for automatic or manual correction of the instrument.

33 Claims, 22 Drawing Sheets

OTHER PUBLICATIONS

Gomm, "Online learning for fault classification using an adaptive neuro–fuzzy network," *Proceedings of the 13th World Congress, International Federation of Automatic Control*, pp. 175–180 (1996).

Aldrich et al., "The use of neural nets to detect systematic errors in process systems," *International Journal of Mineral Processing*, vol. 39, pp. 173–197 (1993).

Hwarng et al., "Back–propagation pattern recognizers for X control charts: methodology and performance," *Computers ind. Engng*, vol. 24, No. 2, pp. 219–235 (1993).

Guo et al., "Identification of change structure in statistical process control," *Int. J. Prod. Res.*, vol. 30, No. 7, pp. 1655–1669 (1992).

Himmelblau et al., "Rectification of data in a dynamic process using artificial neural networks," *Computers chem. Engng.*, vol. 20, No. 6/7, pp. 805–812 (1996).

Sahiner et al., "Feature selection by a genetic algorithm: application to classification of mass or normal breast tissue," *Medical Physics*, vol. 23 (10), (1996).

Deleo, James M., "Receiver Operating Characteristic Laboratory (ROCLAB): Software for Developing Decision Strategies that Account for Uncertainty," *Second International Symposium on Uncertainty Modeling and Analysis*, IEEE, Apr., 1993, 318–325.

Deleo, James M., "The Receiver Operating Characteristic Function as a Tool for Uncertainty Management in Artificial Neural Networking Decision–Making," *Second International Symposium on Uncertainty Modeling and Analysis*, IEEE, Apr., 1993, 141–144.

\* cited by examiner

SYSTEM AND METHOD FOR INTELLIGENT QUALITY CONTROL OF A PROCESS

CROSS REFERENCE TO RELATED APPLICATIONS

This application is a U.S. national stage application of PCT US 98/25182 filed Nov. 24, 1998, which was published in English under PCT Article 21(2), which in turn claims the benefit of U.S. Provisional Application No. 60/066,624 filed Nov. 26, 1997.

FIELD OF THE INVENTION

The invention relates generally to monitoring processes to insure their proper functioning. Such processes include (but are not limited to) acquisition of medical specimen data from laboratory instruments, assembly line manufacturing, and general plant or factory operation. More particularly, the invention describes a two-tiered automated intelligent agent architecture for real-time monitoring of measured values in the process environment to detect and correct unusual and untoward events including catastrophic failure. A secondary use of this invention is as a method for enhancing both human and machine learning, recognizing, and diagnosing untoward events in the process environment as signaled by time-varying behavior patterns of measured values of relevant parameters.

BACKGROUND OF THE INVENTION

Process control ensures that products of a process, whether the products are physical objects or information, are produced correctly. Central to process control is monitoring and assessing measured values in the process, which can be achieved by various computational methods whenever features of a product being produced can be quantified. Through such oversight the process can be corrected to prevent the production of defective products. The problem, however, is how to monitor the process effectively where errors in the process are not readily detectable from the individual products produced (e.g., a laboratory test result). Ideally, the monitoring would detect an error in the process immediately after its appearance, before few defective products are produced. But because of ineffective monitoring, the time between appearance of a process error and its detection is often too long and many defective products may be produced before the error is detected.

For example, the analysis of patient specimens by various clinical laboratory instruments such as chemical analyzers is susceptible to processing errors. These errors can be of several types. Inaccuracy, or analytical bias, occurs if the measured value of patient data systematically deviates from its true value. Imprecision occurs if there is a systematic increase in variability about the true value. And random error occurs when the measured value of patient data differs from the true value non-systematically. Unless these errors are promptly detected and corrected, physicians may receive inaccurate test results, which can lead to misdiagnosis and inappropriate patient management.

A common monitoring procedure for ensuring that clinical laboratory instruments are working properly is to perform all analyses in "batch" mode. (A "batch" is often referred to as a "run".) Patient specimens that are received in the laboratory are saved until enough are collected for a run. The accuracy of the instruments is tested before and after the run by assaying the run control materials which contain known concentrations of the substances being measured. If instrument error is detected, the instruments are adjusted and the specimens are again analyzed before test results are reported.

Batch mode monitoring ensures accurate results, but it is too slow for modern clinical laboratory practice. Patient specimen analysis is frequently required immediately and cannot be postponed until enough other patient specimens are collected for a run. Furthermore, it is not cost effective to test the instruments before and after analyzing individual patient specimens.

Another monitoring approach is to test laboratory instruments periodically (such as every six to 12 hours) with the control materials and adjust the instruments as necessary. This approach allows prompt analysis of patient data, but has the drawback that some patient specimens may be inaccurately analyzed and the results reported before errors are detected.

An alternative to monitoring the quality of laboratory instruments with control material is to monitor them using the test results they generate (see Hoffman, R. G. et al., "The Average of Normals Method of Quality Control," *Am. J. Clinical Pathology*, vol. 105, pp 44–51 (1996)). But except for the daily monitoring of mean test result data, such monitoring is not widely used because current computational methods have limited ability to detect instrument errors from test result data (see Dembrowski, G. S. et al., "Assessment of Average of Normals Quality Control Procedures and Guidelines for Implementation," *Am. J. Clinical Pathology*, vol. 81, pp 492–99 (1984)). The problem with monitoring the daily mean is that it is a retrospective detection method with a long time frame. Potentially a full day of incorrect test results may be reported before such a method detects an instrument failure.

One objective of the invention, therefore, is to provide a practical and cost-effective method and system for detecting errors as they appear (i.e., "in real time") in a general processing environment, before many defective products are produced. An example of such a process to which the invention can be applied is the performance of a laboratory instrument in analyzing patient specimens. Another objective of the invention is to provide such a method and system that utilizes computational methods to analyze process data for identifying the presence of various types of process errors. In the application of this invention to the medical field, problems with laboratory instruments are discovered and corrected before a significant amount of patient data is affected by monitoring test results as they are produced.

SUMMARY OF THE INVENTION

The invention comprises a computer-implemented method for detecting errors in a process such as clinical laboratory data production, assembly line manufacturing, and general assembly plant or factory operations. The method includes the following steps. Data elements having a range of values are collected from the process. The number of data elements having values within predetermined intervals of the range are then counted. The counts of the data elements are applied as inputs to nodes of a neural network, each count being applied to a node representing the predetermined interval corresponding to the count. Output indicative of whether an error has occurred in the process is then generated from the neural network based on the inputs.

In a more specific form of the invention, the step of collecting data elements comprises collecting through a moving window a predetermined number of data elements. The steps of the method are then repeated after moving the window to replace a data element in the window with another newly produced data element outside the window.

In another more specific form of the invention, the method includes the additional step of scaling the data elements to values within a predetermined range before counting the data elements. This scaling step may comprise scaling the data elements to values within the range of zero to one, for example.

In another more specific form of the invention, the neural network is trained to detect a bias error or a precision error in the data elements applied as inputs to the nodes.

Although the invention is applicable to many processes, it is of particular value for detecting errors in the laboratory analysis of patient specimens. When applied to this process, the collecting step comprises collecting test results generated by a laboratory instrument processing patient specimens. The test results are the data elements that are counted, and the counts are applied to the neural network. The neural network monitors trends in test results to detect if the instrument is producing error-free test results. If test results outside of an acceptable range are detected, the neural network output indicates that an error has occurred. The output is generated in real time and available immediately for automatic or manual correction of the instrument. Thus the method substantially eliminates the delay inherent in prior approaches for detecting and correcting laboratory instrument error.

The invention also comprises a system that implements the method.

The foregoing and other objects, features, and advantages of the invention will become more apparent from the following detailed description of a preferred embodiment which proceeds with reference to the accompanying drawings.

DETAILED DESCRIPTION OF A PREFERRED EMBODIMENT

A. Overview

The invention can be used to monitor in real time the performance of any process to determine if that process is working properly. The process must provide a stream of values for various data elements which the invention can monitor and analyze to detect errors in the process. A preferred embodiment of the invention described herein is used for monitoring the performance of a particular process: the analysis of patient specimens by laboratory instruments. It should be understood, however, that the invention can be implemented in any number of embodiments to monitor other types of processes as well.

Figure 1:
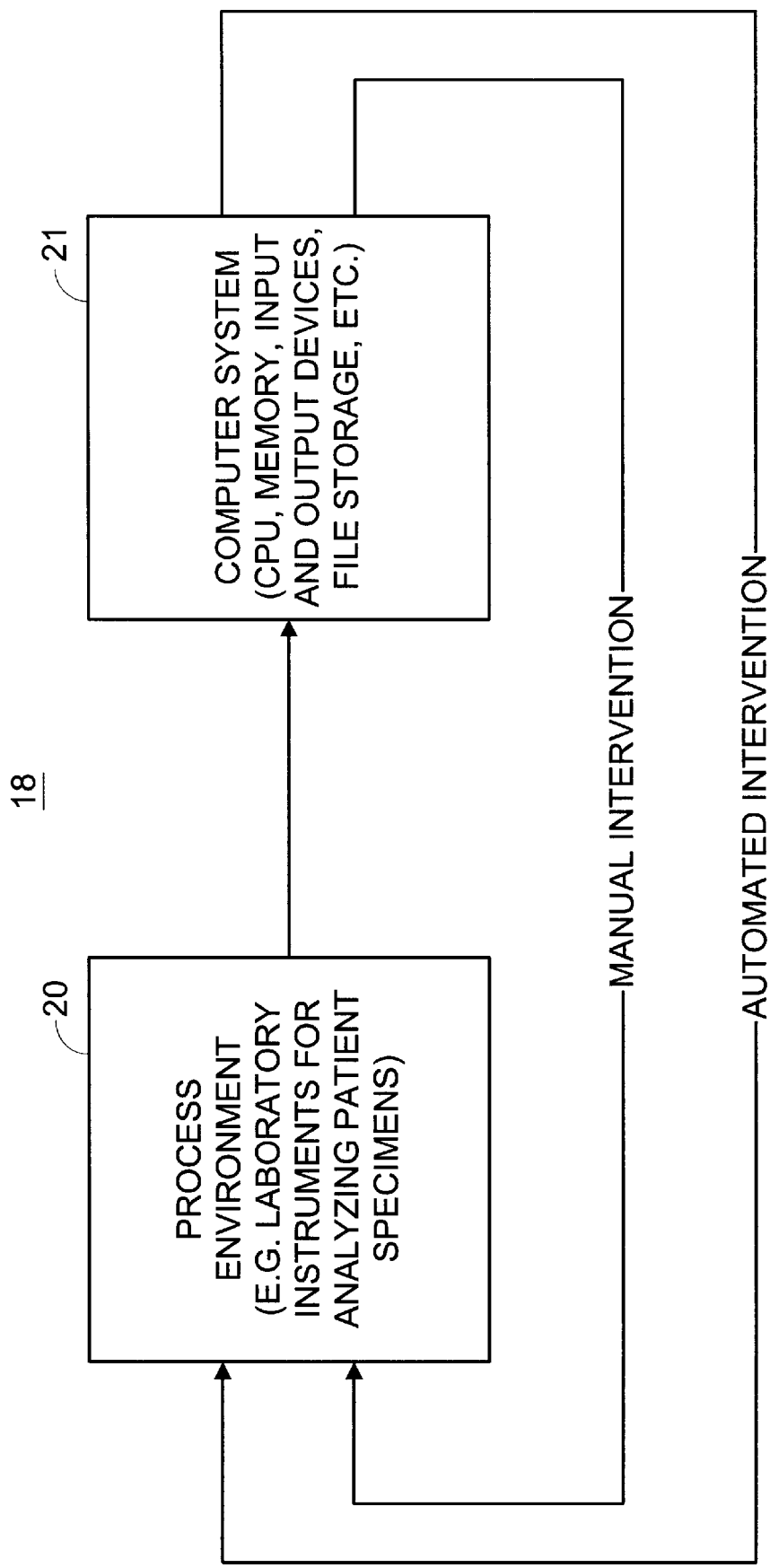
FIG. 1 is a block diagram of a system according to the invention for intelligent quality control of a process.

FIG. 1 is a block diagram of a system 18 according to the invention for intelligent quality control of a process. System 18 includes a process environment 20 and a computer system 21. The process environment includes the reception of process input and the generation of process output, which output is monitored and analyzed in real time by the computer system 21 for determining the quality of the process. More specifically, the computer system 21 is programmed in accordance with the invention to monitor trends in the process output and determine from these trends if an error in the process has occurred. Based on the determination, the computer system 21 provides intervention signals to the process environment 20 to adjust its steps if the process quality is not acceptable. These intervention signals can be automated in the sense that computer system 21 uses it to directly control the operation of the process, or they can be manual in the sense that the computer system alerts a human operator in the process environment to the need for intervention. It should be understood that FIG. 1 is functional and not meant to depict that computer system 21 must be physically separate from the devices that comprise the process environment 20. The functions and components of the computer system can be wholly or partially integrated into the process environment or be a separate device, as desired.

In a preferred embodiment, the invention is used to monitor the performance of laboratory instruments that analyze patient specimens. The process environment 20 in this embodiment includes one or more laboratory instruments that generate a set of test results per specimen (the set being a "data frame" as will be described and each test result being a "data element"). These test result data frames are the "process output" of process environment 20. They are recorded by the instrument in computer-readable form and passed to the computer system 21 for error detection in accordance with the invention. Tile computer system checks trends in test results for errors and based on what it determines generates an intervention signal for adjusting the operation of the laboratory instrument. The manual intervention signal can take many forms, from an audio alarm to a color-based visual alarm. An operator responds to this alarm by making appropriate adjustments to the laboratory instrument. For example, an operator may respond to the alarm signal by testing preassayed quality control material to determine if there actually is an error in the instrument and, if there is, the operator would perform instrument recalibration or maintenance as necessary. The automated intervention signal, if employed, directly controls the adjustment of the laboratory instrument.

In accordance with the invention, the computer system 21 can be a separate system from the laboratory instrument. However, it is envisioned that the functions of computer system 21 can be incorporated into the laboratory instrument through an embedded data processor or equivalent device and accompanying software or firmware.

B. Details of the System and Method

Figure 2A:
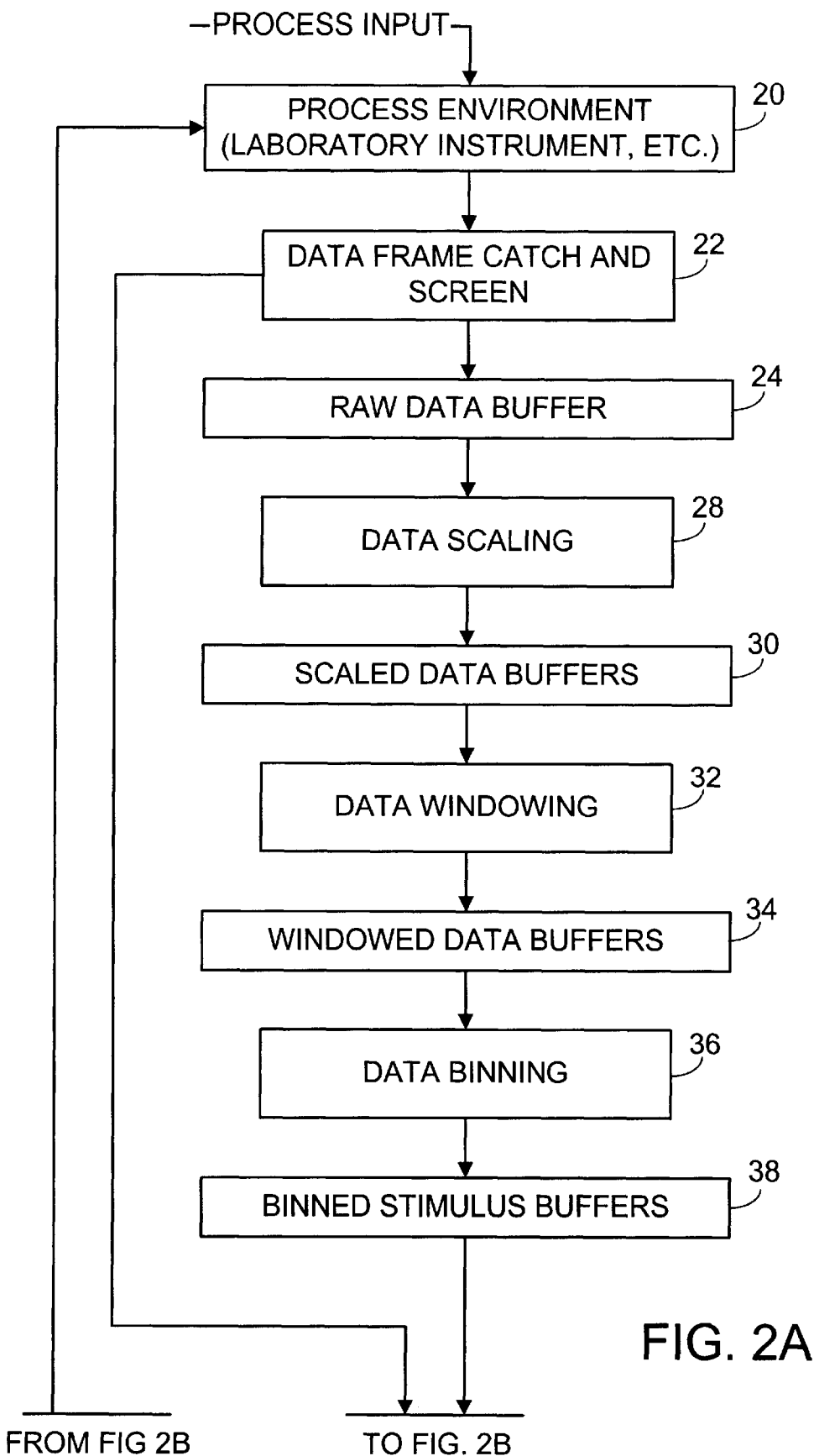
FIGS. 2A and 2B are two parts of a block diagram illustrating a method according to the invention for detecting errors in a process.
Figure 2B:
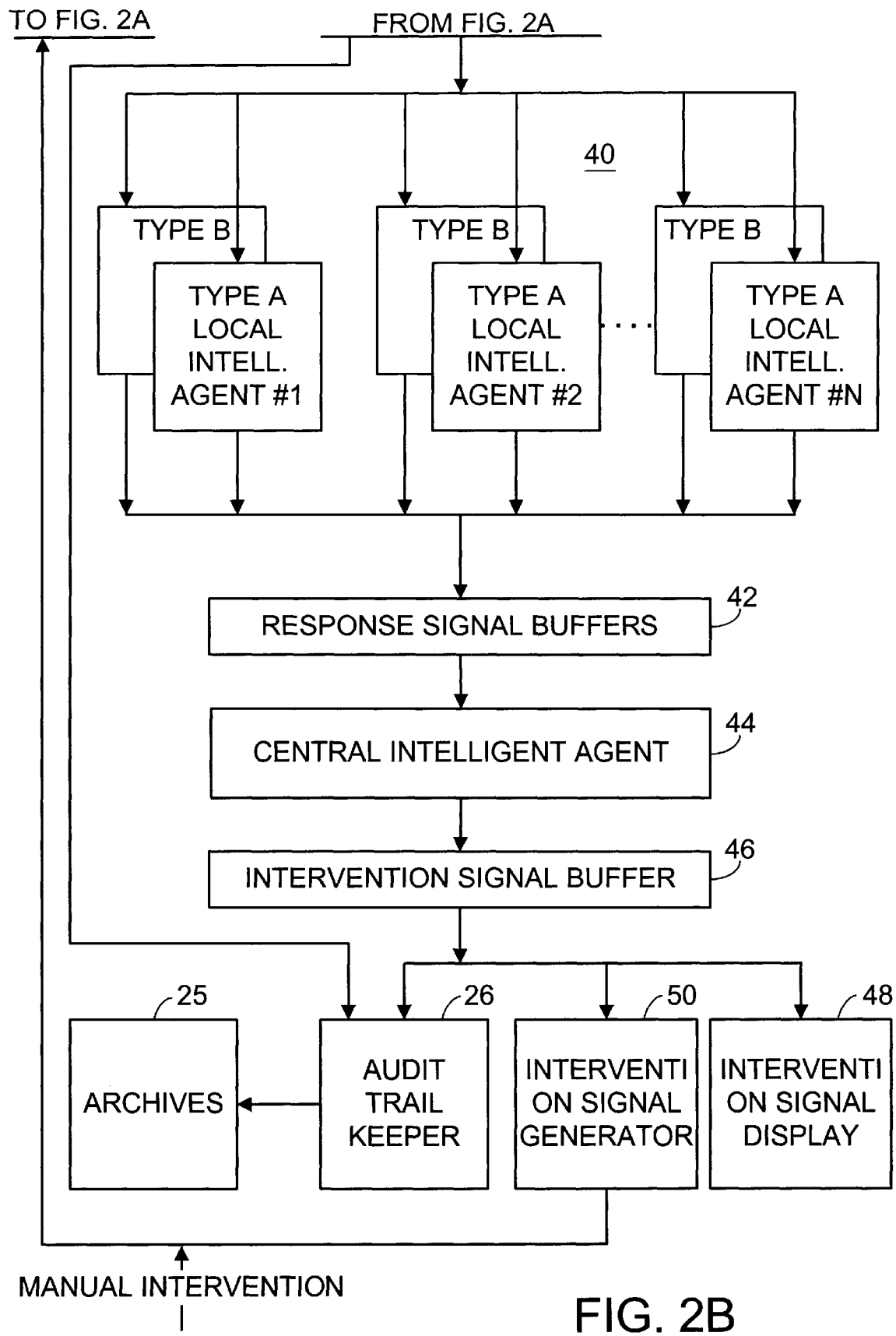

FIGS. 2A and 2B are two parts of a block diagram illustrating a method according to the invention for detecting errors in a process environment. The figures begin with process environment block 20 in FIG. 2A and continue with an alternating series of computational steps and data storage (buffers) for storing the results of the previous computation. The figures end with intervention signal blocks 48 and 50 in FIG. 2B.

1. Catching and Screening Data Elements

Referring to FIG. 2A, the process environment 20 generates a full or partial frame of data. In a preferred embodiment of a process for analyzing patient specimens, the specimens are provided as input to an instrument such as an automated general chemistry analyzer. This instrument analyzes a patient's serum and produces a set of test results, or analyte values, for blood levels of calcium, sodium, potassium, glucose, etc. The data frame for each specimen represents a set of such test results, each set associated with a different patient specimen. The data elements within each frame represent the individual test result values.

Figure 3:
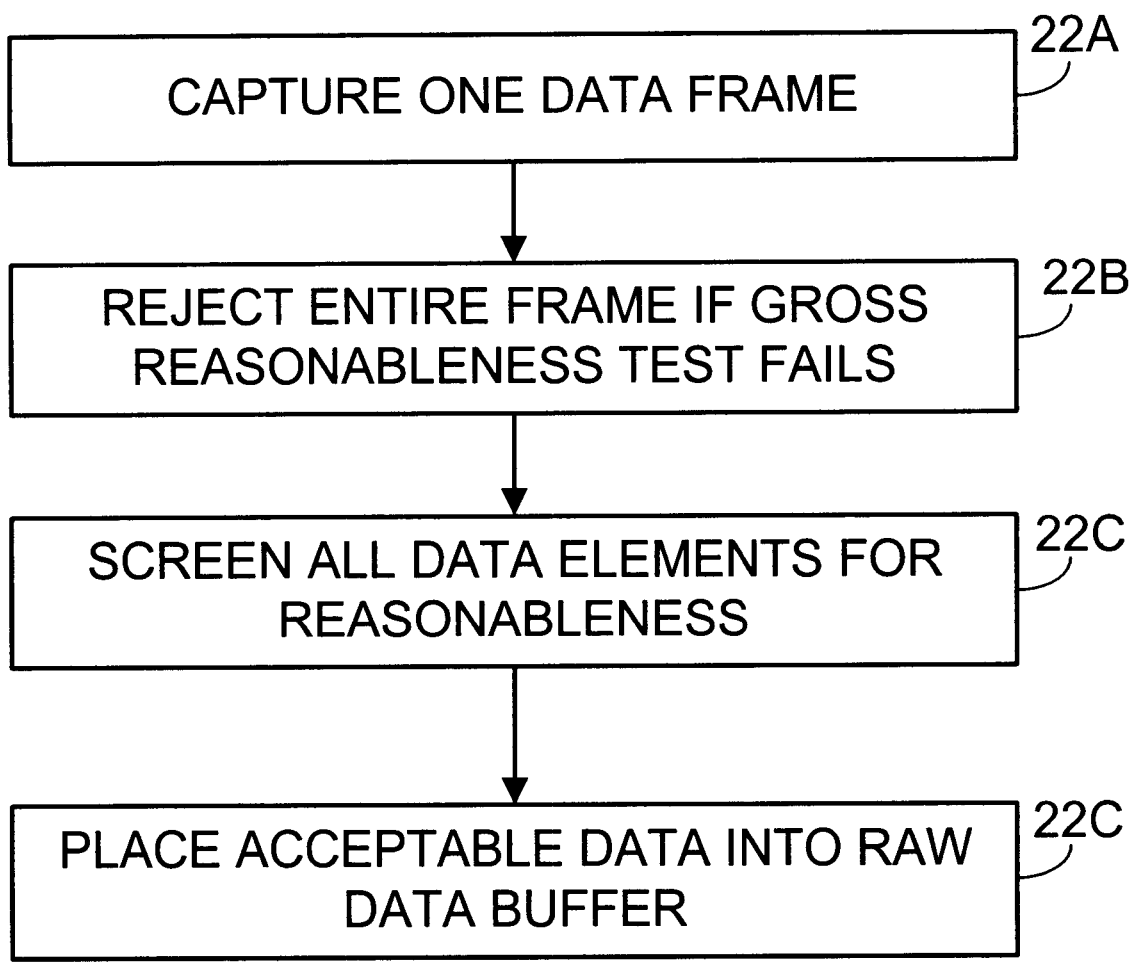
FIG. 3 is a now chart of a method for catching and screening data in accordance with the invention.

The data frames from the process environment 20 are directed to a data frame catch and screen computational module 22, which represent computational steps performed on the data. Referring to FIG. 3, as a first step a data frame is captured (22a). The entire data frame is checked for a gross level of reasonableness (22b). It is then checked to determine if individual data elements in the frame appear are "reasonable" (22c). Data elements outside a predetermined range ("unverified data") are removed from the data frame and the rest ("verified data") are placed in a raw data buffer 24 (22d). All data elements (verified and unverified) are stored in an archive 25 by means of an "audit trail keeper" computational module 26 (FIG. 2B). Identifiers for unverified data are posted in an error log for later review.

2. Scaling, Windowing, and Binning

The data elements in a raw data buffer 24 are read by a data scaling computational module 28 that scales each data element onto a predetermined interval such as the unit interval scale [0,1] for each data error type being monitored.

Figure 4:
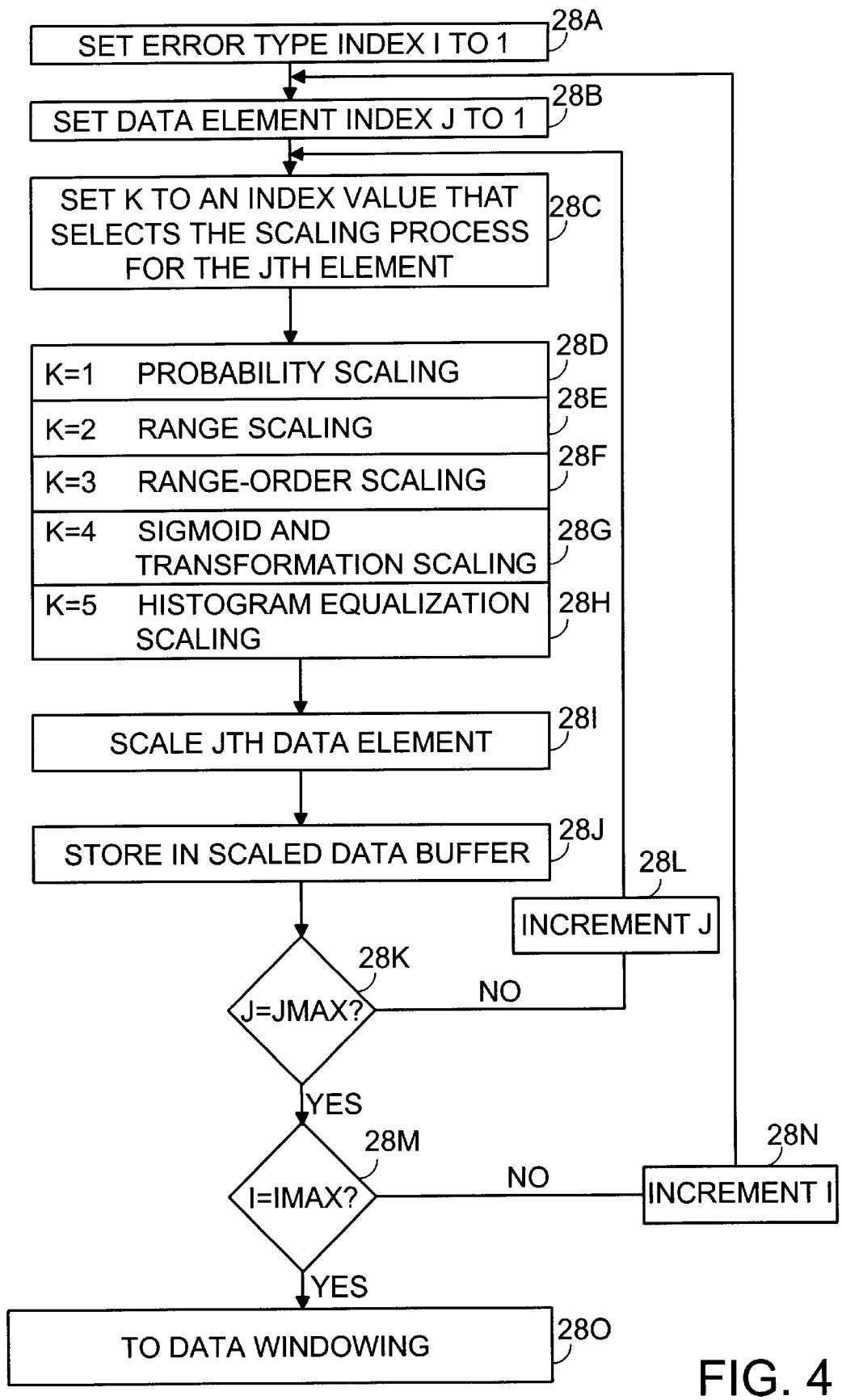
FIG. 4 is a flow chart of a method for scaling data in accordance with the invention.

FIG. 4 shows how this scaling works for each error type, I. The error type index I is set to 1 (28a). A counter for the number of data elements, J, in the frame is initialized to 1 (28b) and a scaling technique is selected according to the K counter (28c). The scaling technique presently can be probability scaling (28d), range scaling (28e), range-order scaling (28f), sigmoid transformation scaling (28g), or histogram scaling (28h). Other scaling techniques may also be used. The data element is then fetched from the raw data buffer 24, scaled in accordance with the selected scaling technique (28i), and stored in a scaled data buffer 30 (28j). If this element is not the last element in the raw data buffer (28k), then the J counter is incremented (28l) and the next data element is processed until the last data element in the buffer 24 is fetched, scaled, and stored. If the current error type is not the last error type (28m). then the I counter is incremented (28n) and scaling for each data element is performed until scaling for the last error type is completed. The scaled data is then passed to the data windowing computational module 32 (28o).

Figure 5:
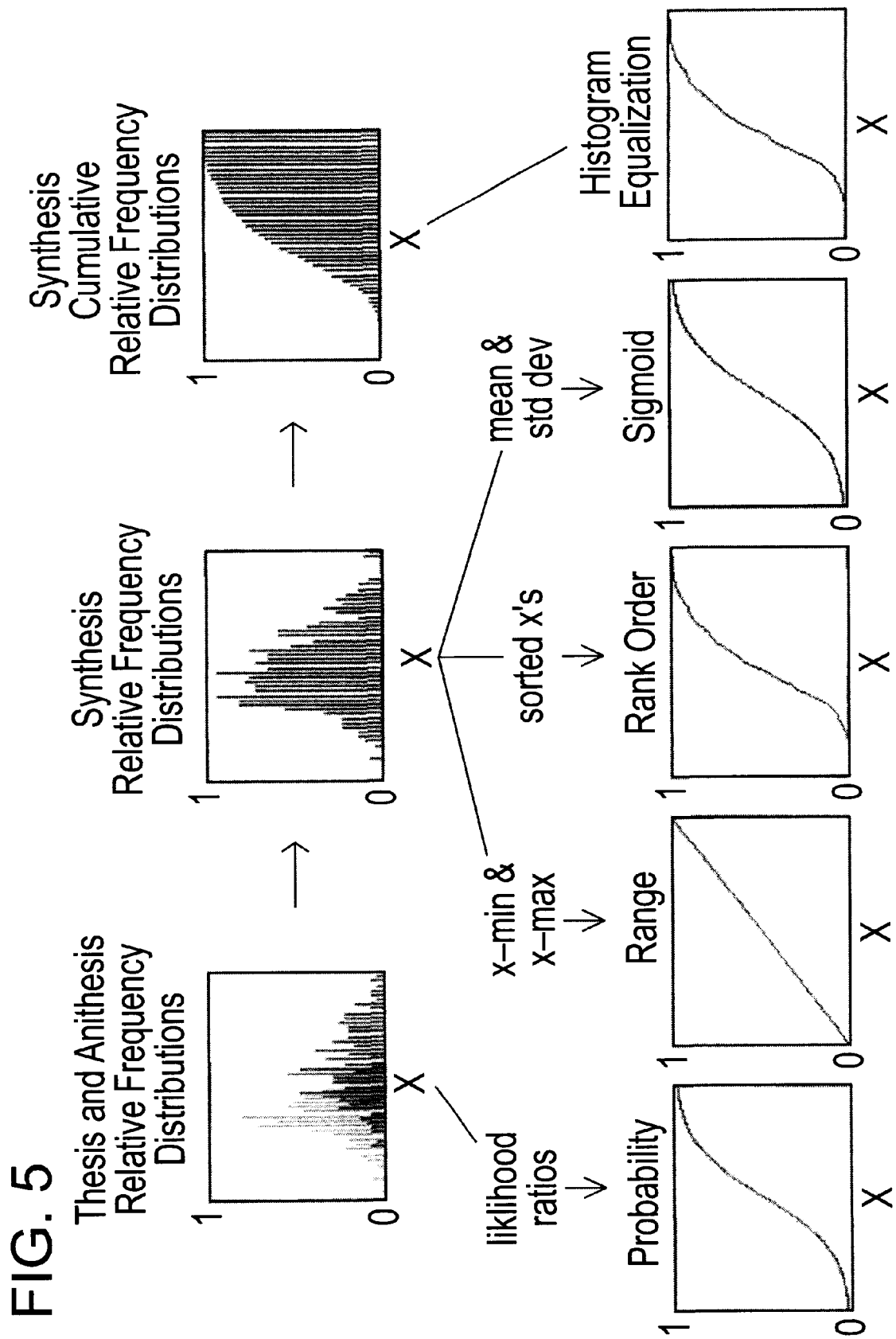
FIG. 5 illustrates possible scaling procedures for use in the scaling method.

FIG. 5 illustrates five scaling methods that may be used. Each scaling method is applicable to each type data element, but certain scaling methods perform better for particular kinds of errors being monitored. For example, it is anticipated that histogram equalization scaling will perform best for bias shift errors and probability scaling will perform best for precision errors.

It can be seen in FIG. 5 that probability scaling is based on likelihood ratios computed directly from the raw data found in the error-free (thesis) and error (antithesis) distributions. Range, rank order, and sigmoid scaling are accomplished by drawing on certain properties of the synthesis distribution, i.e., the combined thesis and antithesis distributions. And histogram equalization scaling is performed using the synthesis cumulative relative frequency distribution. All these scaling methods map input values x to some value on the 0–1 interval.

The method of the invention can check for several types of errors such as low bias, high bias, and precision loss (incremented variance). For each type of error to be detected, each data element is scaled separately. For example, the data elements can be subjected to range scaling for low bias, to sigmoid transform for high bias, and to probability scaling for precision loss. The scaled data elements are then stored by data element type and error type in separate data buffers 30.

Figure 6:
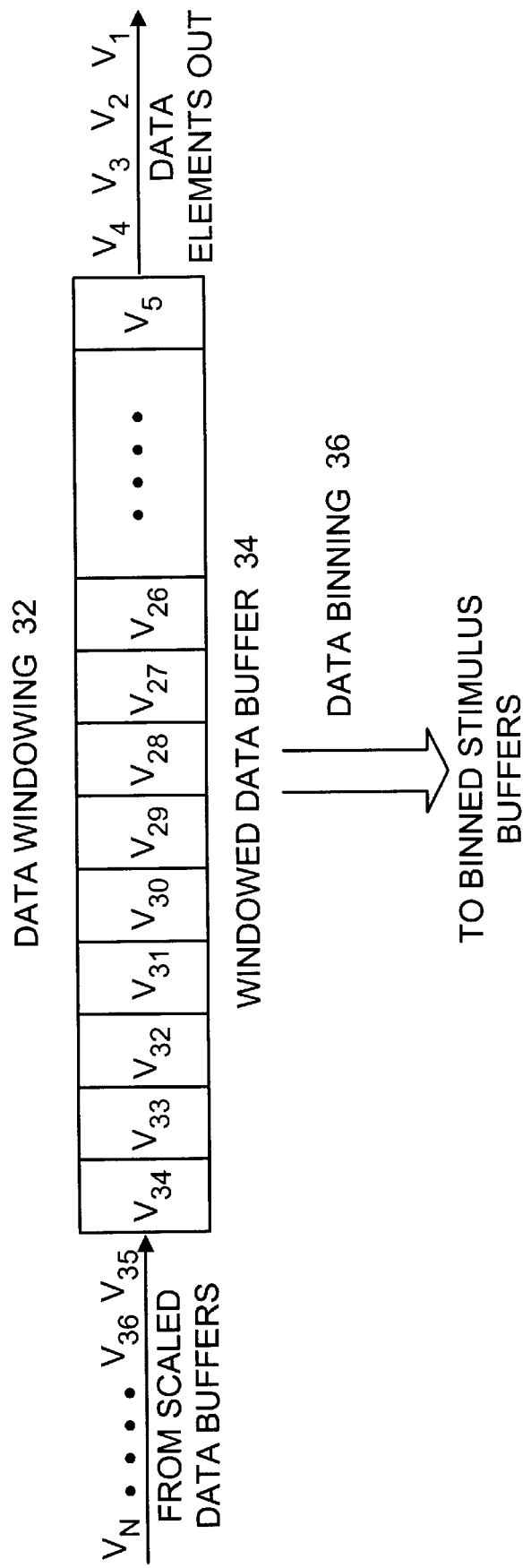
FIG. 6 illustrates a method for windowing and binning data for evaluation in accordance with the invention.

FIG. 6 is a block diagram of a how the data windowing and data binning computational modules work to process the scaled data. "Windowing" refers to a feature in which the latest succession of some fixed number (the window length) of scaled data element values is processed by a local intelligent agent to assess the membership of these values in the (positive) error population. The data window module 32 reads scaled data elements from scaled data buffer 30 and passes these data elements to a set of moving window data buffers 34. Since each unique combination of error type and data element type (e.g., laboratory test value type) can have a specified scaling process, each such combination must have a unique associated window data buffer and local intelligent agent. Each window data buffer holds a time-sequenced string of data elements for a particular data element type scaled for a particular error type. The number (window size) of data elements in each of these buffers is also specified uniquely for each window according to predetermined standards of accuracy in detecting errors for the particular combination of error type and data element type.

For example, a scaled data buffer 30 may contain 3 sets of 25 data elements, such as individual laboratory test values for blood levels of calcium, sodium, potassium, glucose, etc. associated with an individual patient. The three sets could correspond to low bias error, high bias error, and precision loss error. The windowing computational module 32 transfers each of the 75 (3×25) scaled data elements to the appropriate one of the corresponding 75 window buffers in a first in first out (FIFO) queuing manner. The FIFO queue is illustrated in FIG. 6 in which data element $V_{34}$ enters the queue of a window buffer of length 30 as data element $V_4$ exits the queue.

The new data set is then read from the windowed data buffer 34 by the data binning computational module 36, as indicated by the arrow. Buffer 34 thus operates to provide a data element set that captures trends in data changes by changing one data element each time the data value set is evaluated. The FIFO queue, of course, is only one of many possible forms that buffer 34 may take. Data elements can be discarded from other locations in the window and in groups of one or more, depending on the desired implementation. Furthermore, the size of the window may be varied to meet error detection accuracy requirements of the particular embodiment. A larger window generally provides more accuracy in detecting errors in a process. But the tradeoff is that a larger window requires more time for detection of a possible instrument failure, thus delaying the system response.

On start up of the method, the data window buffers 34 are initialized with dummy data elements of reasonable error-free values. These dummy data elements are gradually pushed out of the buffers 34 as actual real time scaled data elements are serially written into them.

After a new data element is shifted into a buffer 34, the data binning computation module 36 counts the number of data elements (now scaled) in each data element set which fall within predetermined intervals of the range [0,1]. For example, the buffer 34 contains a set of 30 data elements at any given time, scaled to values from 0 to 1. Assume that there are 100 equal predetermined intervals (or bins) ranging from 0.00–0.01 to 0.99–1.00. Each interval is represented by a storage location in a binned stimulus buffer 38. The data binning computational module stores the counts corresponding to all scaled data values in a window in the corresponding buffer locations. These counts indicate the distribution of the data elements over the range of possible values. When a new data element is shifted into the window buffer 34, the data binning computation module 36 generates a new set of counts.

A buffer 38 exists for each type of error and for each type of data element. In the example above wherein three types of errors are detected and 25 types of data elements exist, there are 75 binned stimulus buffers 38.

Figure 7:
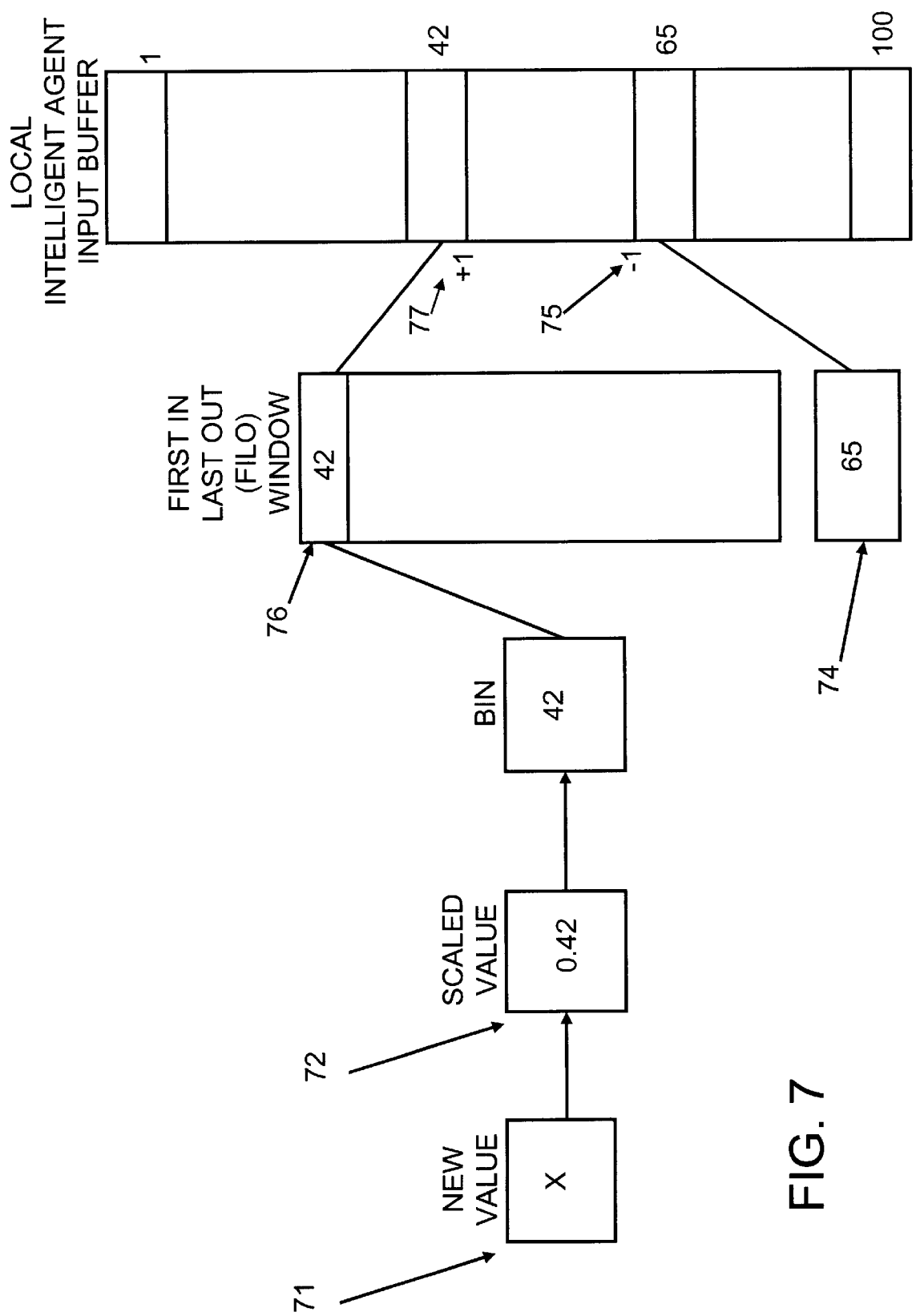
FIG. 7 is a block diagram showing the combined operations of scaling, windowing, and binning in accordance with the invention.

In operation, the scaling, windowing and binning operations operate in tandem as follows: the bin associated with the newest scaled value is determined, and its bin count is incremented, the bin associated with oldest scaled value is determined, and its bin count is decremented. The scaling, windowing, and binning operations are illustrated in FIG. 7. A new value 71x directed to a particular local intelligent agent is scaled onto the 0–1 unit interval as 0.42 72 and added to the moving window 76, forcing out the oldest data element 74 having a value of 0.65. The count for the bin associated with the 0.42 value 77 is then incremented and the count for the bin associated with the 0.65 value 77 is decremented. These counts are updated in the local intelligent agent input buffer. The buffer of the local intelligent agent is now ready for evaluation by the local intelligent agent.

Figure 8:
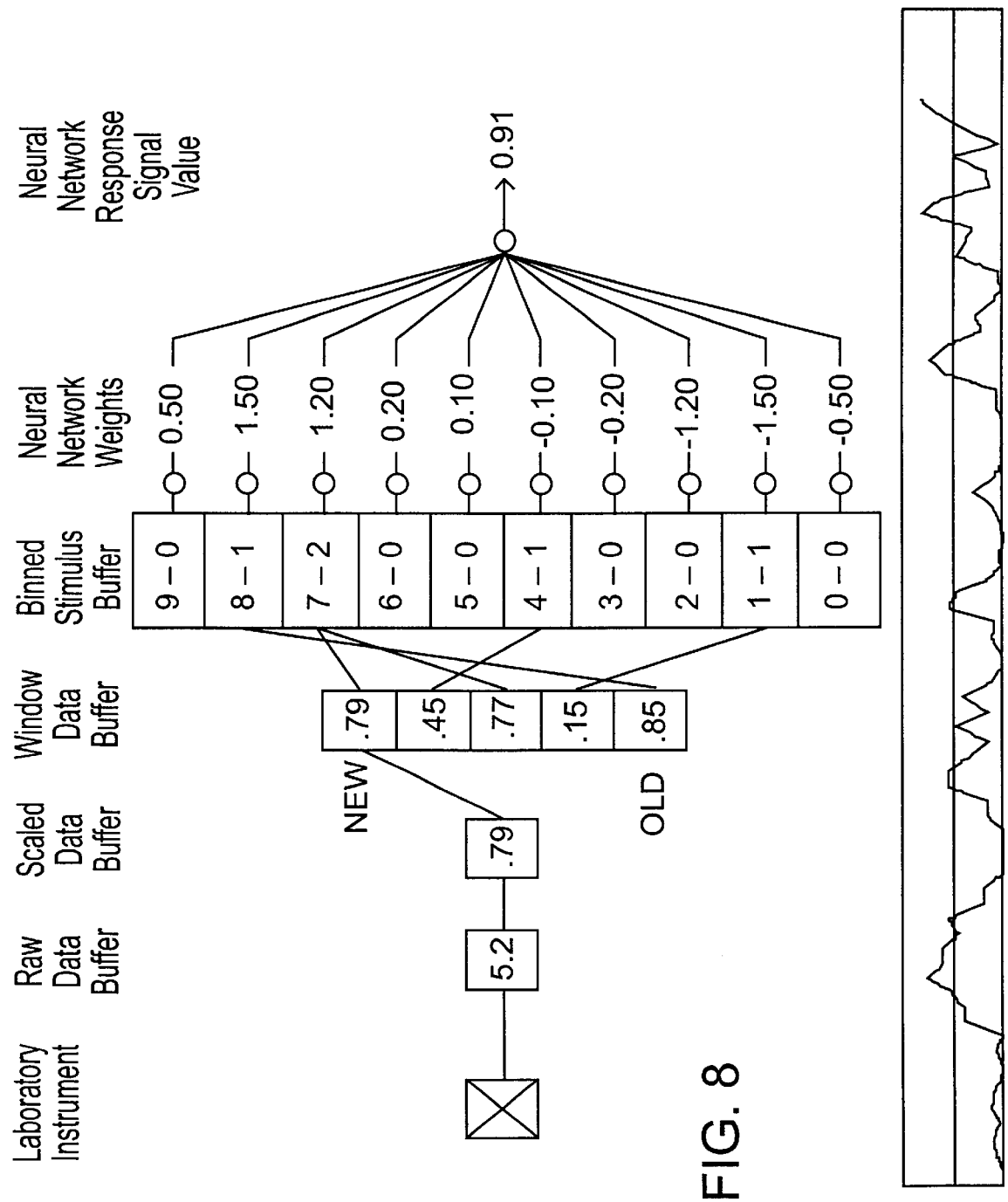
FIG. 8 is a block diagram showing the combined operations of scaling, windowing, binning and decision making by a local intelligent agent in accordance with the invention.

FIG. 8 illustrates the flow of events starting with the arrival of a new data element through to the output of a neural network-based local intelligent agent. In this illustration the window size is five, the number of bins is 10, and the local intelligent agent is a no hidden layer back error propagation neural network. In the preferred embodiment, window sizes are likely to be in the 20 to 30 range, number of bins 100, and local intelligent agents either no hidden layer or hidden layer back error propagation neural networks or other neural networks.

In FIG. 8, the value of a new data element is scaled, the scaled value is placed in the window data buffer, and bin counts are appropriately updated. A no hidden layer back error propagation neural network computes the weighted sum of the input bin counts and "squashes" this sum onto the 0–1 unit interval. The equations for these neural network computations are respectively as follows:

$$s = \sum_{i=1}^{10} w_i x_i \quad (1)$$

$$p = \frac{1}{1 + \exp(-s)} \quad (2)$$

in which $w_i$ is the neural network weight associated with the $i^{th}$ node, $x_i$ is the bin count value associated with the neural network node, and p is the probability, or more generally the fuzzy possibility that the windowed data belongs to the error class.

3. Local Intelligent Agents

The buffers 38 are read by local intelligent agents 40 (FIG. 2B) that correspond to the different types of error detected and individual data elements.

The local intelligent agents in the present embodiment are computational modules embodied in software, firmware, or hardware. Other embodiments are, of course, possible. These agents are designed to perform simple, clearly-defined tasks. Intelligent agents may be trained through learning from examples (e.g., neural networks), or they are pre-programmed by means of established artificial intelligence methodologies (e.g. rule-based inferencing).

The term "local intelligent agents" is chosen to emphasize the localized nature of the task performed by this type computational module, which is to evaluate a parameter with respect to an error (such as testing for cholesterol with respect to high bias error). The resulting signals output from the local intelligent agents are passed to a central intelligent agent 44, where decisions about altering the process environment are made. This broad design in which local intelligent agents report to a central intelligent agent is an example of "subsumption architecture" in the domain of computer science referred to as "artificial intelligence." The subsumption architecture of the present invention is such that the intelligent processing of raw signals performed by the local intelligent agents enhances intelligent classification of the data as acceptable or unacceptable, thereby relieving the central intelligent agent of these more basic tasks. Thus, the central intelligent agent can be designed to focus on the task of deciding what action should be performed based on the input from the many individual local intelligent agents. Subsumption architectures such as this often exhibit "emergent properties" which are useful behaviors not explicitly considered and planned for in the original design.

As shown in FIG. 2B, multiple tiers of intelligent agents may used in embodiments of the invention. These tiers include the local intelligent agents 40 and the central intelligent agent 44. The local intelligent agents have the specific task of assessing the performance of one process environment parameter with respect to one kind of error. These agents "amplify" the parameter values as "signals" that are useful in detecting occurrences of particular types of errors. The central intelligent agent is the focus or center to which all of the local intelligent agents report their individual findings. The task of the central intelligent agent is to translate these findings into actions that will effect positive changes in the process environment when necessary.

In the present embodiment there are two types of local intelligent agents: Type A and Type B. Type A agents are designed to detect time-sequenced, systematic bias and precision errors associated with a single parameter. Type B agents are designed to detect random single parameter errors which may occur spontaneously (i.e., non-systematically) at any point in time in single frames of data. All output values from these local intelligent agents are placed into a set of response signal buffers 42, which are the input buffers to the central intelligent agent 44.

Type B local intelligent agents are designed to detect random single parameter errors which may occur spontaneously (i.e. nonsystematically) at any point in time. The task of a Type B agent is to give an indication of how far off a particular parameter value is with respect to what it is predicted to be from other parameter values in the present data frame as well as from certain other historical data. Type B agents may be implemented as machine learning paradigms such as neural networks, or as more classical artificial intelligent paradigms such as rule based systems. For example, in the monitoring of patient laboratory data, using a neural network to predict a patient's measured analyte value from other analyte values for the same patient may be useful in detecting nonsystematic errors. An example of a rule-based approach would be to apply rules based on monitoring of the anion gap, which is currently performed in most general chemistry analyzers. Type B agents may be trained and tested with historical data similar to Type A agents.

Several agents 40 of each type are shown in FIG. 2B to illustrate that the error detection may occur with parallel computing architecture in which each computing agent is assigned the task of evaluating the degree of membership a window of particular data element holds in a particular error class. The output of each agent indicates how the most recent window of data elements it processed is performing with respect to the type of error the agent is designed to detect.

The clinical laboratory process environment in which an embodiment of this invention is in use includes two laboratory instruments, each of which produces up to 25 test results per specimen at a maximum rate of one specimen per minute. Each test value may be examined for as many as four different error types including low bias, high bias, precision loss, and random errors. Thus 200 different local intelligent agents may be required by each of which would produce results at the rate of one per minute for a combined overall rate of 200 results per minute. A system such as this in which overall data throughput is not so demanding, is easily implemented on a small, state-of-the-art, single processor, Von Neumann-type computer system. In environments having more devices, higher data rates, more parameters, and more error types where much higher overall data throughput is required, local intelligent agents may be embodied as a set of parallel processors.

Figure 9:
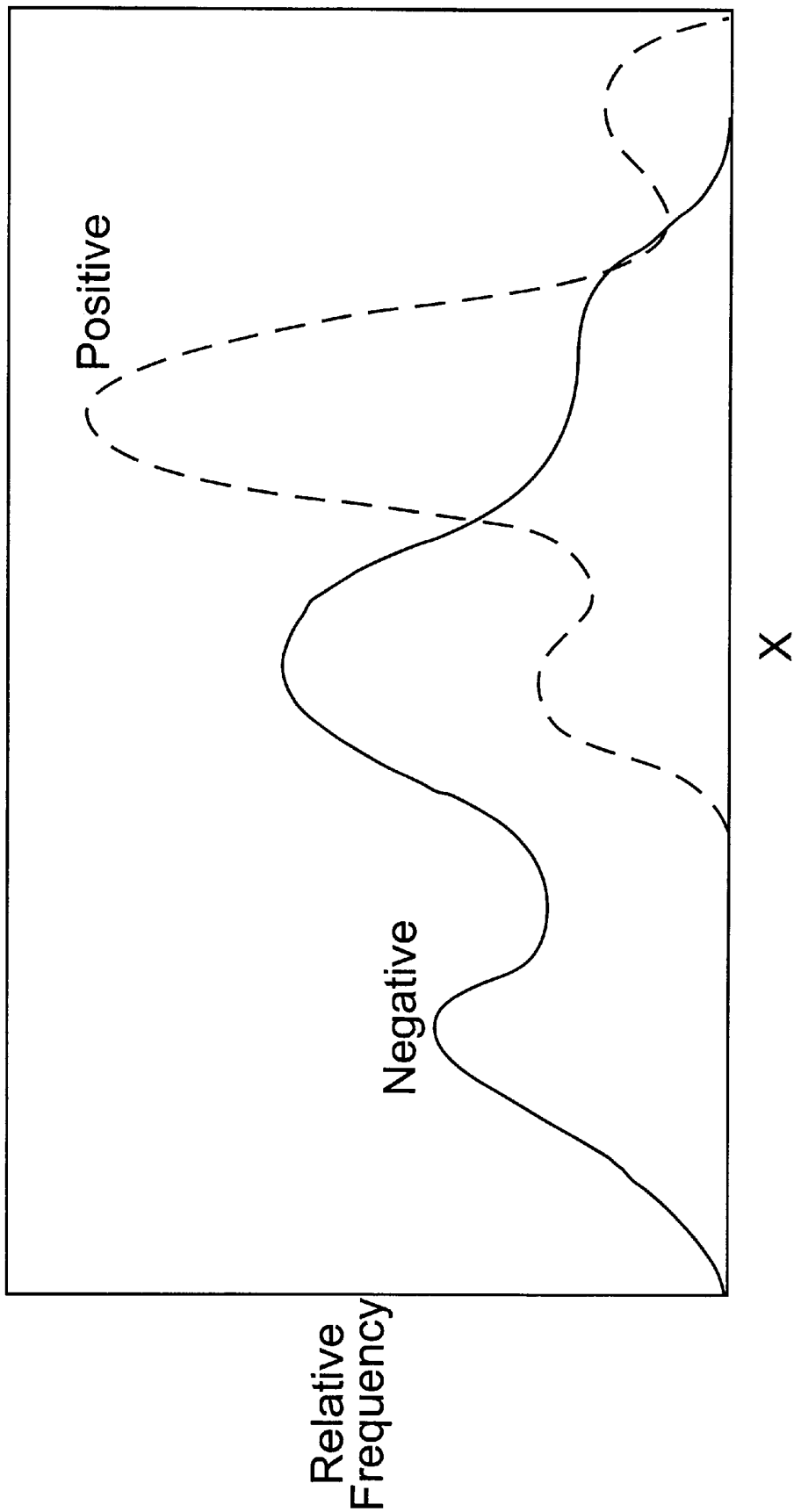
FIG. 9 is a chart illustrating two generalized contrasting dichotomous data populations.

The task of a type a local intelligent agent is to differentiate clusters (time windows) of sampled data that are acceptable in the sense that they fail to fulfill some criteria for belonging to a particular error class, or not acceptable, in the sense that they do fulfill the criteria. In general then, it is the task of this agent to differentiate two distinct, dichotomous populations as the source of the windowed sampled data clusters. FIG. 9 depicts two generalized contrasting dichotomous data populations. To generalize even further, each local intelligent agent is designed to output a degree of membership values d, on the [0,1 ] interval, with d interpreted according to Table 1:

TABLE 1

| | Population A | Population B |
|---|---|---|
| $d = 0$ | full membership | full non-membership |
| $0 < d < 1$ | partial membership, $1 - d$ | partial membership, $d$ |
| $d = 1$ | full non-membership | full membership |

Although the labeling of Population A and Population B is arbitrary, the convention is to label as Population B the "positive" population which is usually the one to be detected. The convention is to consider outcomes associated with Population A as "negative" events and those with B as "positive" events. In the present application the positive events would be the erroneous, unacceptable data.

Figure 10:
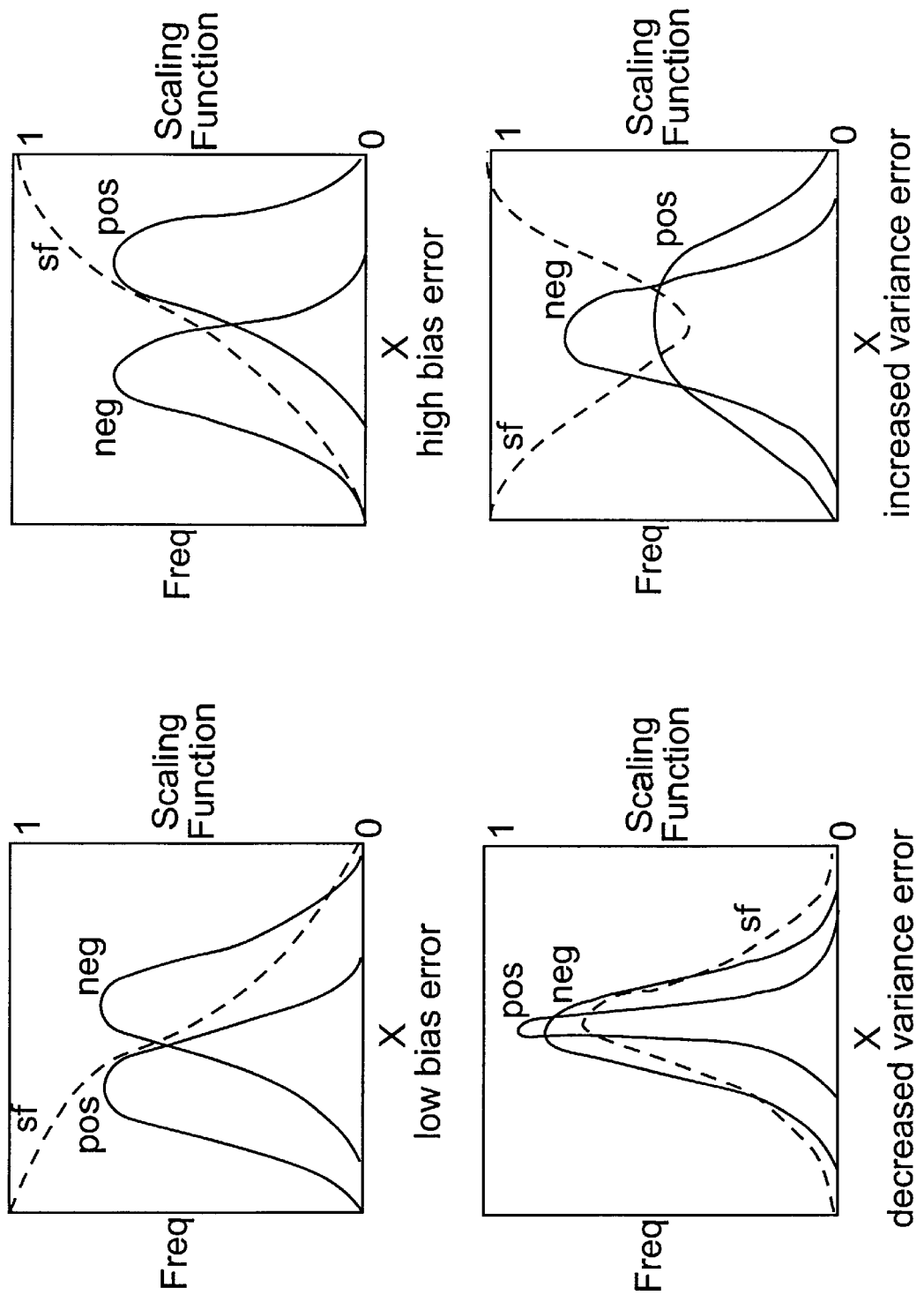
FIG. 10 is a series of graphs illustrating the nature of different types of process errors detectable by the method and system of the invention.

Although the invention is broad enough to include differentiation of robust dichotomous populations as depicted in FIG. 9, the present embodiment differentiates more well behaved populations related to what is referred to here as "bias errors" and "variance errors" the latter being also being referred to as "precision errors." These errors are depicted in the FIG. 10. Bias errors occur when an instrument malfunctions in such a way as to produce values that are either too low (low bias) or too high (high bias) with respect to the true values. Variance or precision errors occur when the instrument malfunctions in such a way as to decrease or increase (precision loss) the overall variance of test values.

Figure 11A:
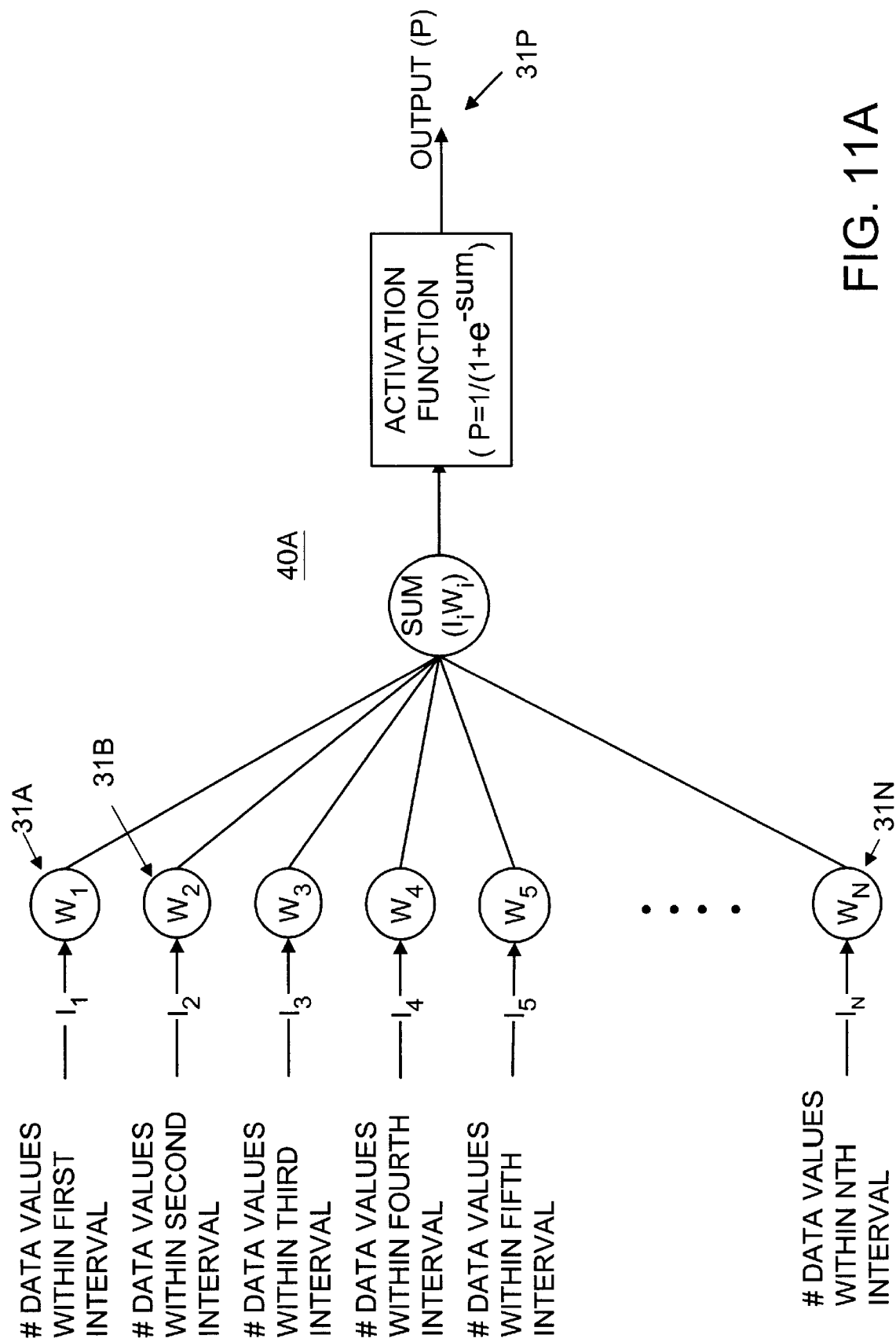
FIG. 11a is a block diagram of a single layer neural network embodiment of a local intelligent agent in FIG. 2B.
Figure 11B:
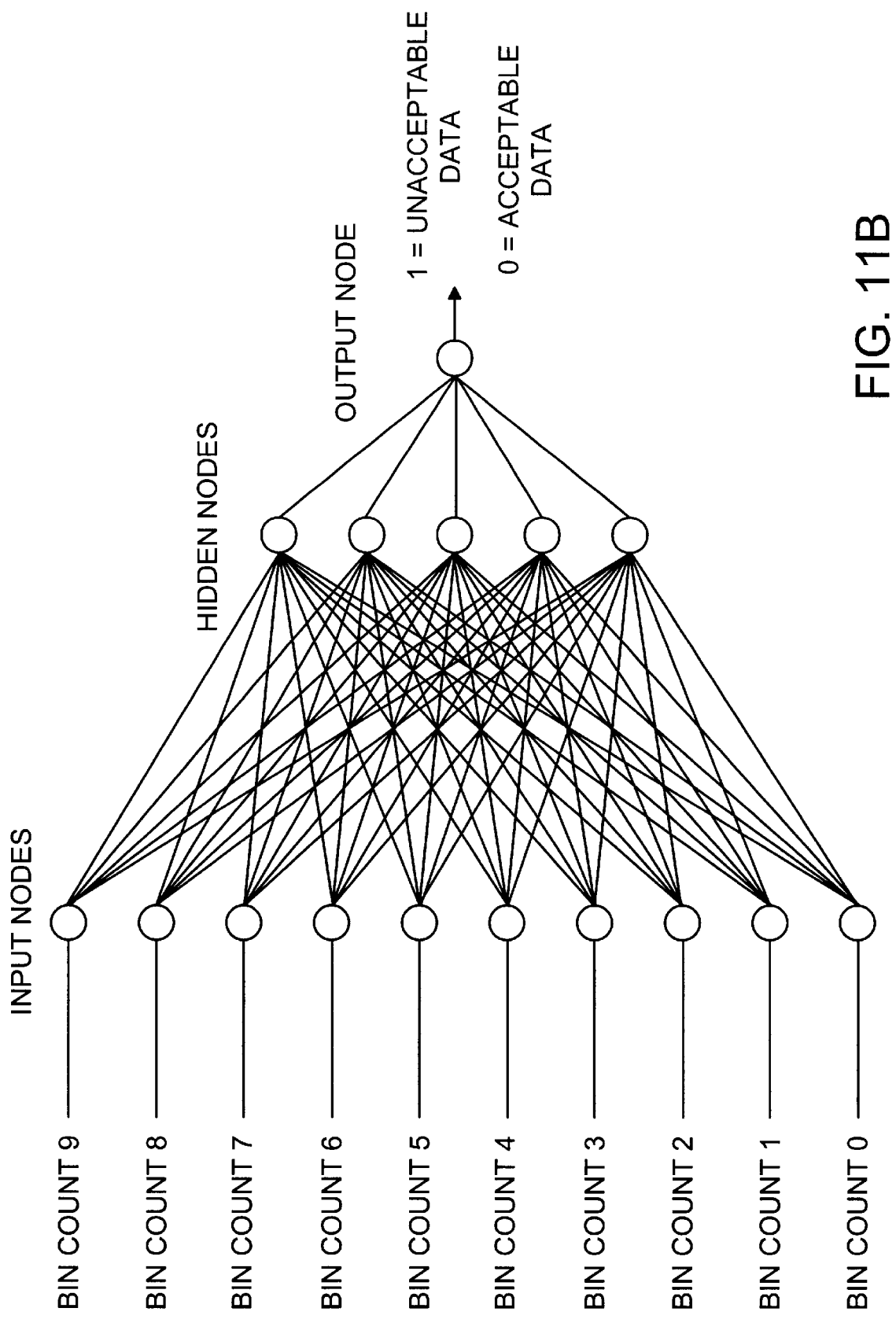
FIG. 11b is a block diagram of a multiple layer neural network embodiment of a local intelligent agent in FIG. 2B.

FIGS. 11a and 11b illustrate how a local intelligent agent 40, when embodied as a single or multiple layer neural network, works to detect an error in the process environment 20. The interval counts from a binned stimulus buffer 38 are applied as inputs to the agent 40 (in this embodiment, to the nodes of neural network agent 40a). The agent produces a signal value in response that indicates the degree to which an error has been detected. The agent 40 then stores this signal value in a response signal buffer 42 (one for each agent) and alerts the system that the signal is available, such as by setting a flag. The details of the structure and operation of a preferred neural network embodiment is described below.

4. The Central Intelligent Agent

The task of a central intelligent agent is to interpret or "make sense" of the large array of signals it receives. Each signal is reporting the relationship of one parameter to one of four basic error types, namely low bias, high bias, low precision, and random errors. The role of the central intelligent agent is to translate these signals into actions that will change the environment in some fashion. Initially, the central intelligent agent is best embodied as an artificial intelligent rule-based module that will post its findings on a display monitor and sound an alarm when adverse events are detected. This module could become a self-adaptive module by learning while performing in the real-time process environment.

All response signals stored in each buffer 42 are read by a central intelligent agent 44. This agent is preferably a computational module that enhances these response signals so that a more accurate determination of error can be made.

The central intelligent agent 44 enhances signals by adjusting them in the following manner:

$$p'(i) = \frac{R(i)p(i)}{1 + [R(i) - 1]p(i)} \quad (3)$$

in which p'(i) is the adjusted signal value for the $i^{th}$ parameter, p(i) is the unadjusted value, and R(i) is the product of the likelihood ratio values associated with prevalence and misclassification costs. A more detailed explanation of this signal enhancement is given in the following description of ROC methodology.

The central intelligent agent 44 also stores threshold warning values for all enhanced signals. Intervention signals based on a comparison of adjusted p-values with these threshold values, are passed to an intervention signal buffer 46. From there, the intervention signals are passed to an intervention signal display module 48, an intervention signal generator module 50, and the audit trail keeper module 26.

Figure 12:
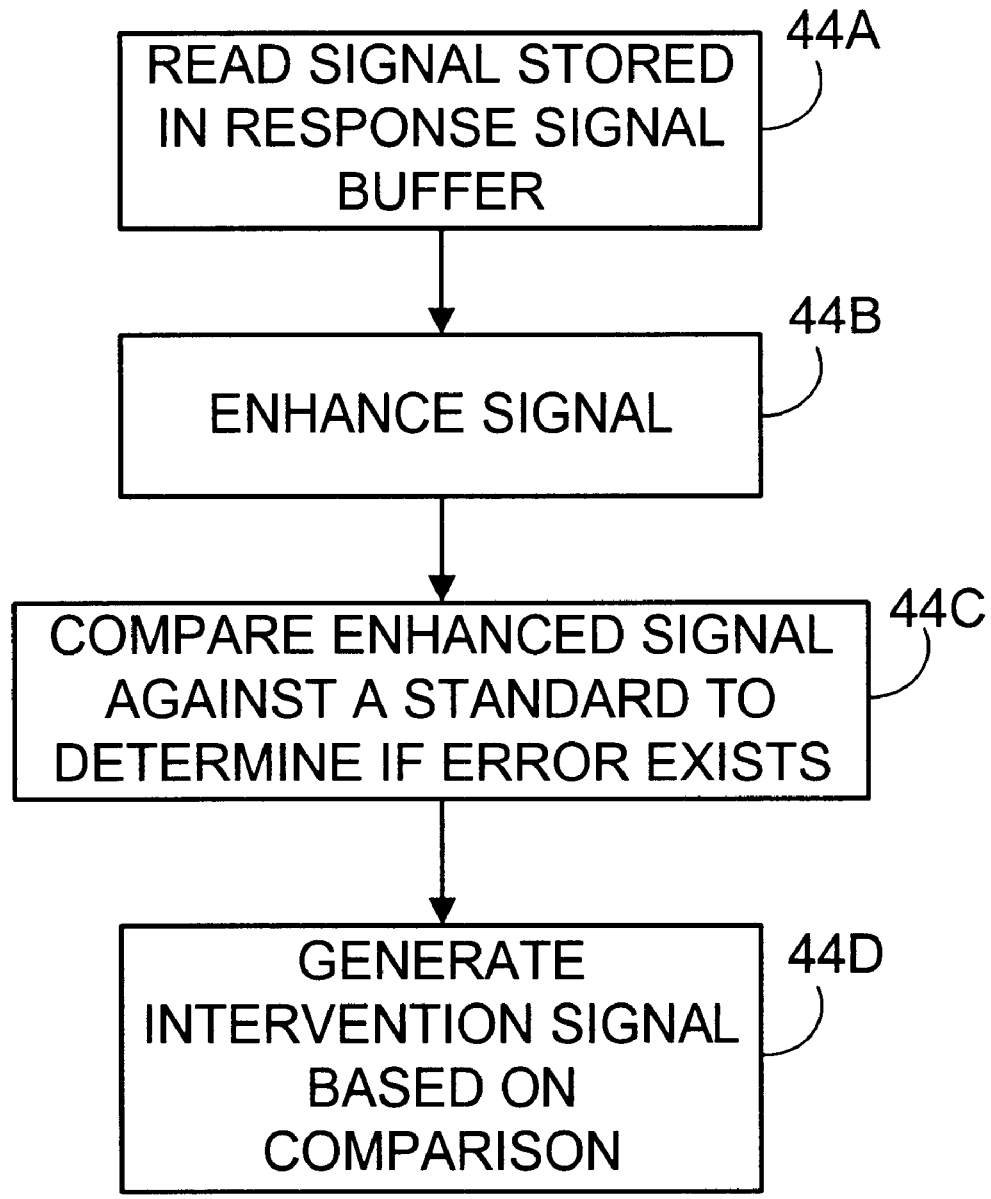
FIG. 12 is flowchart of a method in accordance with the invention for detecting a process error by examining the output of the local intelligent agents in FIG. 2B.

The general operation of the central intelligent agent 44 is shown in the flow chart of FIG. 12. The agent reads a response signal from a buffer 42 (44a) and enhances it (44b). The enhanced signal is then compared against an appropriate threshold warning value (44c), and an intervention signal is generated based on that comparison (44d).

Figure 13:
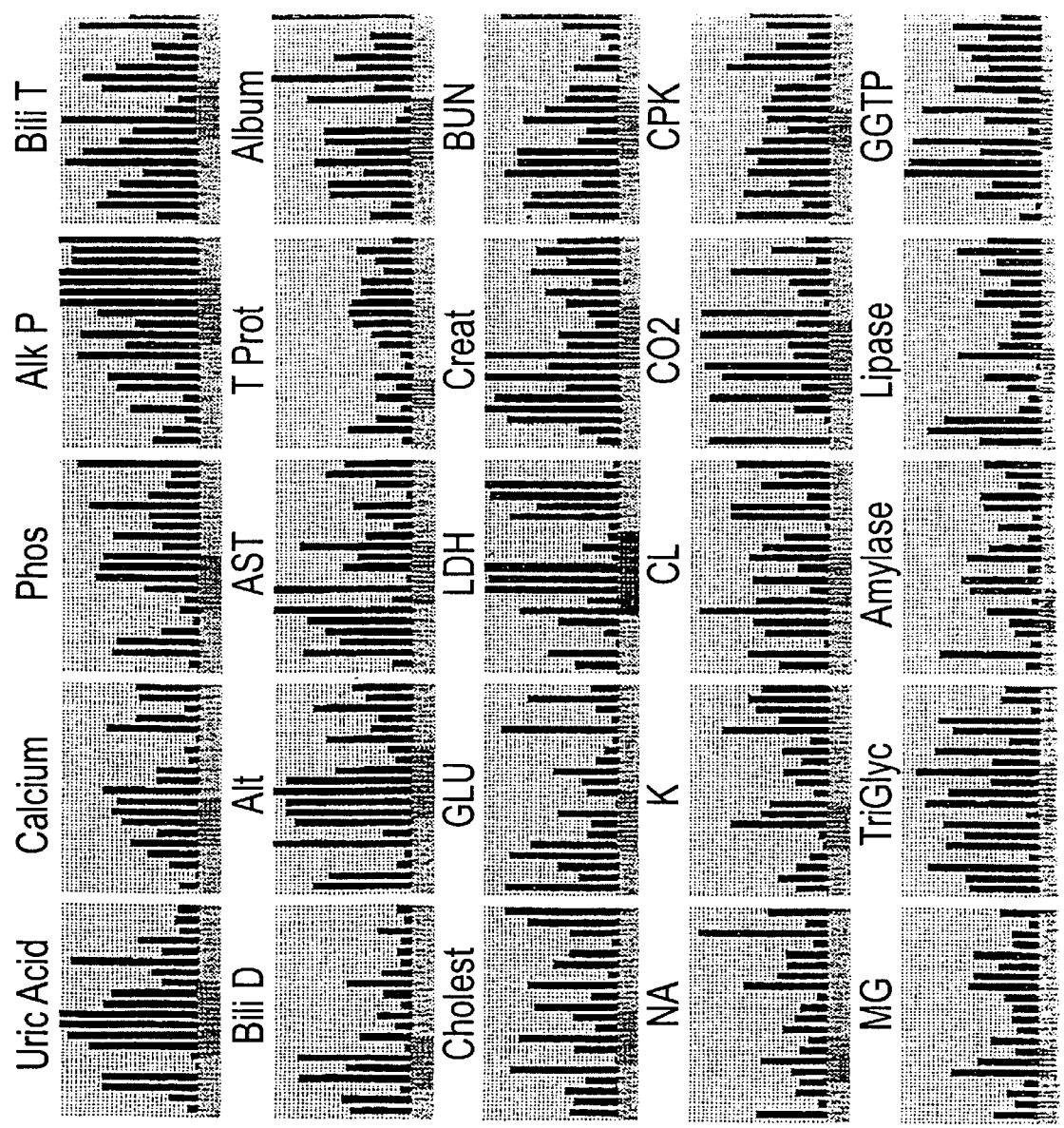
FIG. 13 is a first graphic display indicating if a process error has been detected.
Figure 14:
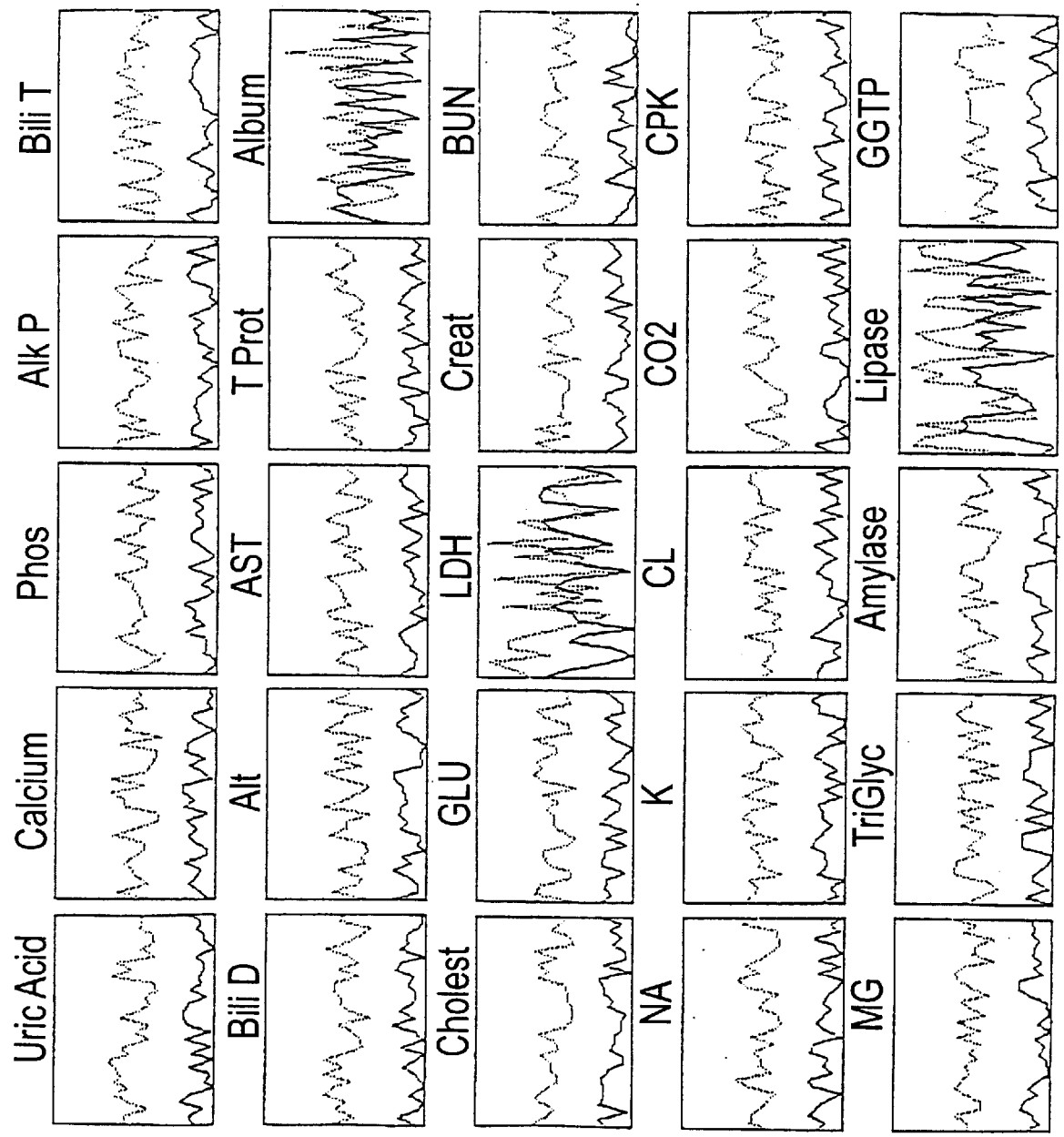
FIG. 14 is a second graphic display indicating if a process error has been detected.

The role of the intervention signal display module 46 is to transform the intervention signals into visual and auditory alert signals that can be conveyed to a system operator. In a preferred embodiment, the module 46 conveys these visual and auditory signals to a computer display monitor and to sound generation hardware, respectively. Two types of display screens have been designed. FIG. 13 shows a graphic display of raw data element values for the various tests result along with a visual bar that indicates which of the values may be erroneous. FIG. 14 shows a graphic display of intervention signal values along with visual and auditory alert signals. These display screens are updated each time a new data element is processed by the method.

The intervention signal generator module 50 makes intervention signals available to other instruments that automatically control the process environment 20. These "automated intervention" signals may be provided in analog or digital form, as desired by the system designer or required by the process devices (e.g., laboratory instruments with multiple adjustment controls).

The method is continually repeated with new data until the system is halted. The audit trail keeper module 26 archives all raw and processed data for later off-line review and analysis in archive 25. For example, off-line processing modules may be employed to perform statistical analysis on the archived data.

5. Exemplary System

Figure 2C:
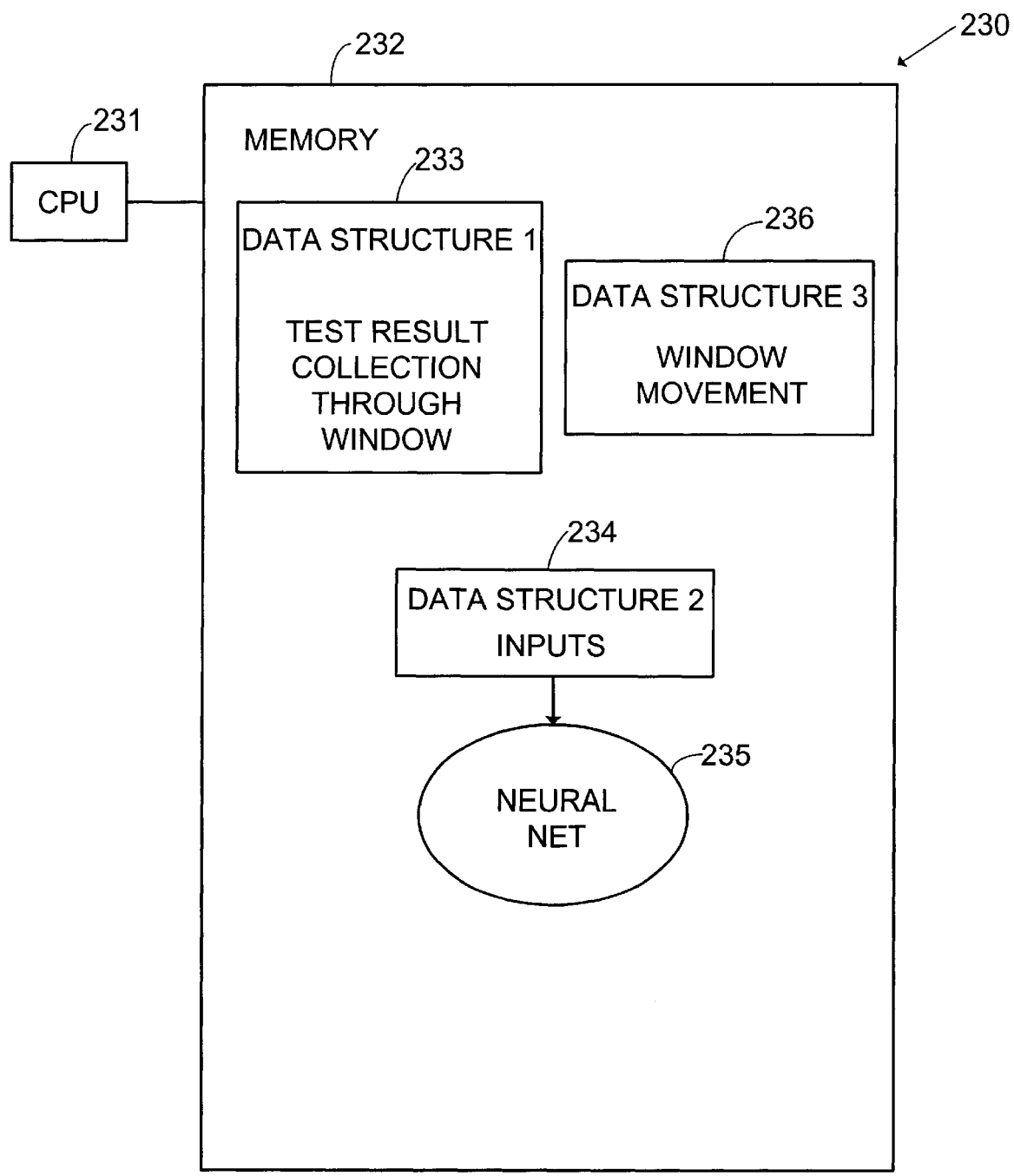
FIG. 2C illustrates an exemplary system for detecting errors in the analysis of patient data.

FIG. 2C shows an exemplary system 230 for detecting errors in the analysis of patient data. The system comprises a central processing unit 231, a memory device 232 coupled to the central processing unit 231. The memory device 232 includes a first data structure 233, a second data structure 234, a neural network 235, and third data structure 236.

The first data structure 233 is for collecting through a moving window a number of test results from a number of patients. The second data structure 234 is for applying the test results as inputs to nodes of a neural network (e.g., the neural network 234).

The neural network is for generating an output based on the inputs applied to its nodes, the output indicative of whether an error in the analysis of patient specimens has occurred. And, the third data structure 236 is for moving the window to replace a test result in the window with another test result outside the window. The neural network 235 can generate additional outputs as the test results in the window change.

The system 230 can include a laboratory instrument for analyzing patient specimens and generating test results therefrom. In the system 230, the neural network 235 can be trained to detect a bias or precision error in the test results applied as inputs to its nodes. The neural network 235 can be a multilayer network trained with a back-propagation algorithm. The nodes of the neural network 235 can correspond to intervals of test result values.

The second data structure 234 can include a counter for counting the number of test results having values within predetermined intervals of the range of values and applying the counts of test results as inputs to the nodes of the neural network 235, each count being applied to a node representing the predetermined interval corresponding to the count.

The second data structure 234 can include means for scaling the test results to values within a predetermined range before counting the test results.

C. Training of The Local Intelligent Agents

Local intelligent agents are trained in the "off-line" manner described next. However, a more advanced future embodiment could employ continuous "on-line" agent training.

To train local intelligent agents off-line for their task of differentiating clusters (windows) of data samples drawn from two contrasting data populations, sample data sets representative of the two populations are needed. These data sets may be collected directly from the process environment 20. Ordinarily, error conditions in the processor environment occur rarely. In such cases, it is more practical to hypothesize the kind of distortion a data element would be subjected to in the failed state and to use the hypothesis to generate a contrasting faulty data set. If, for example, the distortion was a high bias shift of 10%, the erroneous data set could be generated by simply shifting each data element in the error-free sample by 10%. Similar operations could be performed for low bias and precision distortions as well.

For clarity, an original "clean" data set is hereafter referred to as the "thesis data" and a "distorted," "erroneous," or "contrasting" data set is referred to as the "antithesis data". Thus the initial tasks required to produce training data for local intelligent agents are to first produce thesis and antithesis data sets, and then to combine and sort these data sets and use the final sorted data set to produce a unitary interval [0,1] scaling conversion table. The individual sorted thesis and antithesis data sets are used to randomly draw window-sized samples for local intelligent agent training and the scaling conversion table is used to convert samples to the unitary interval and then to bin numbers. The scaling conversion table produced during training is used for the same purposes in the on-line production system.

Figure 15:
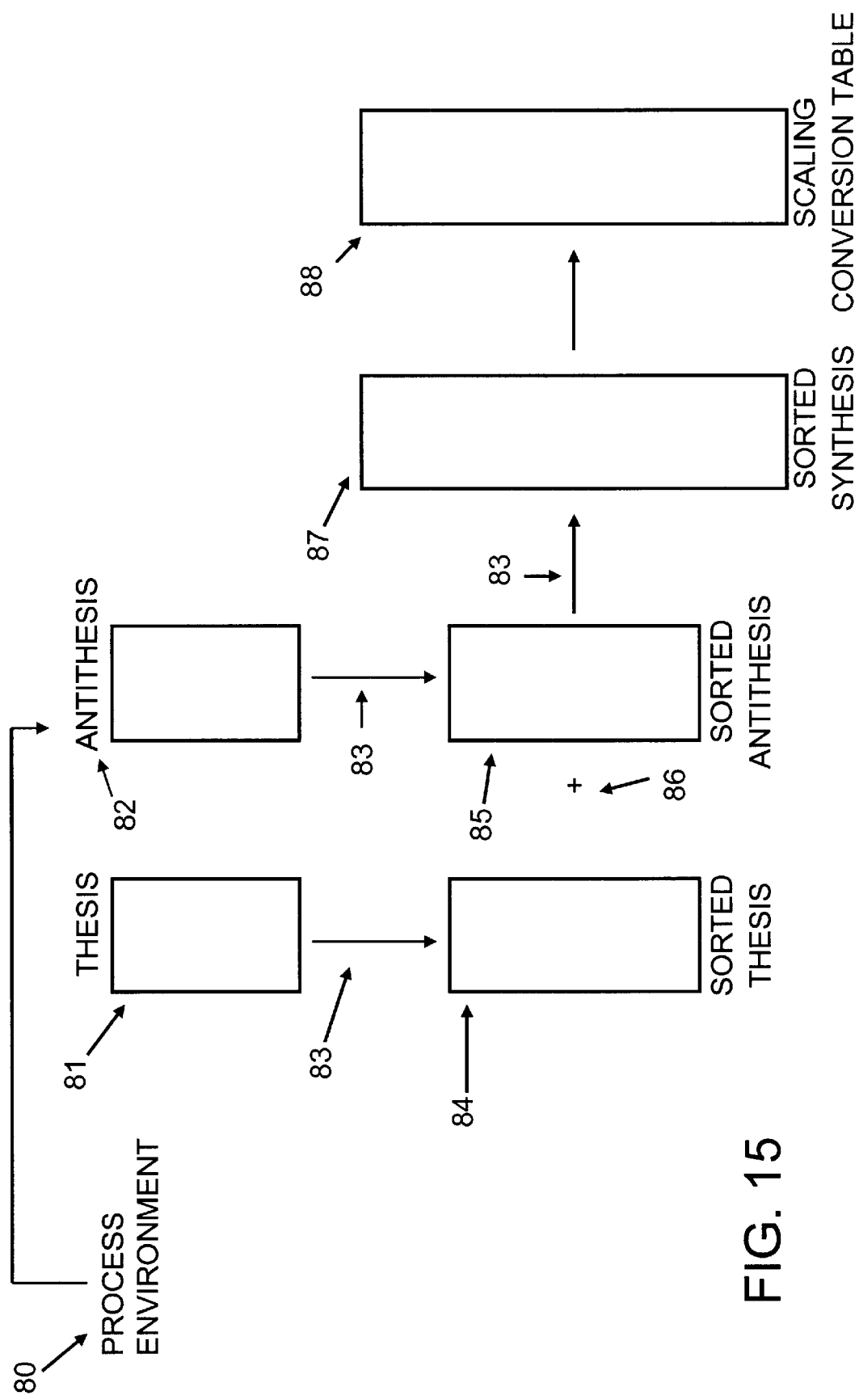
FIG. 15 is a block diagram of a method in accordance with the invention for producing two contrasting sets of training data for training of local intelligent agents.

FIG. 15 illustrates the steps to produce two contrasting data sets (thesis and antithesis) and a unitary interval data scaling conversion table. A significant sample (2000 values or more) of error-free, thesis data 81 is collected from the process environment 80 when it is operating in a normal error-free mode. Similarly, a significant sample of erroneous, antithesis data 82 is collected from the process environment 80 when it is operating in a state to produce erroneous data. If it is not possible to collect antithesis data directly from the process 80, the antithesis data 82 is produced from a hypothesized model. Next, the thesis data 81 is sorted 83 to produce the sorted thesis data 84 and the antithesis data 82 is sorted 83 to produce the sorted antithesis data 85. Then, the sorted thesis data 84 and the sorted antithesis data 85 are combined 86 and sorted 83 to produce sorted synthesis data 87 which in turn is used to produce a unitary interval scaling conversion table 88.

Figure 16:
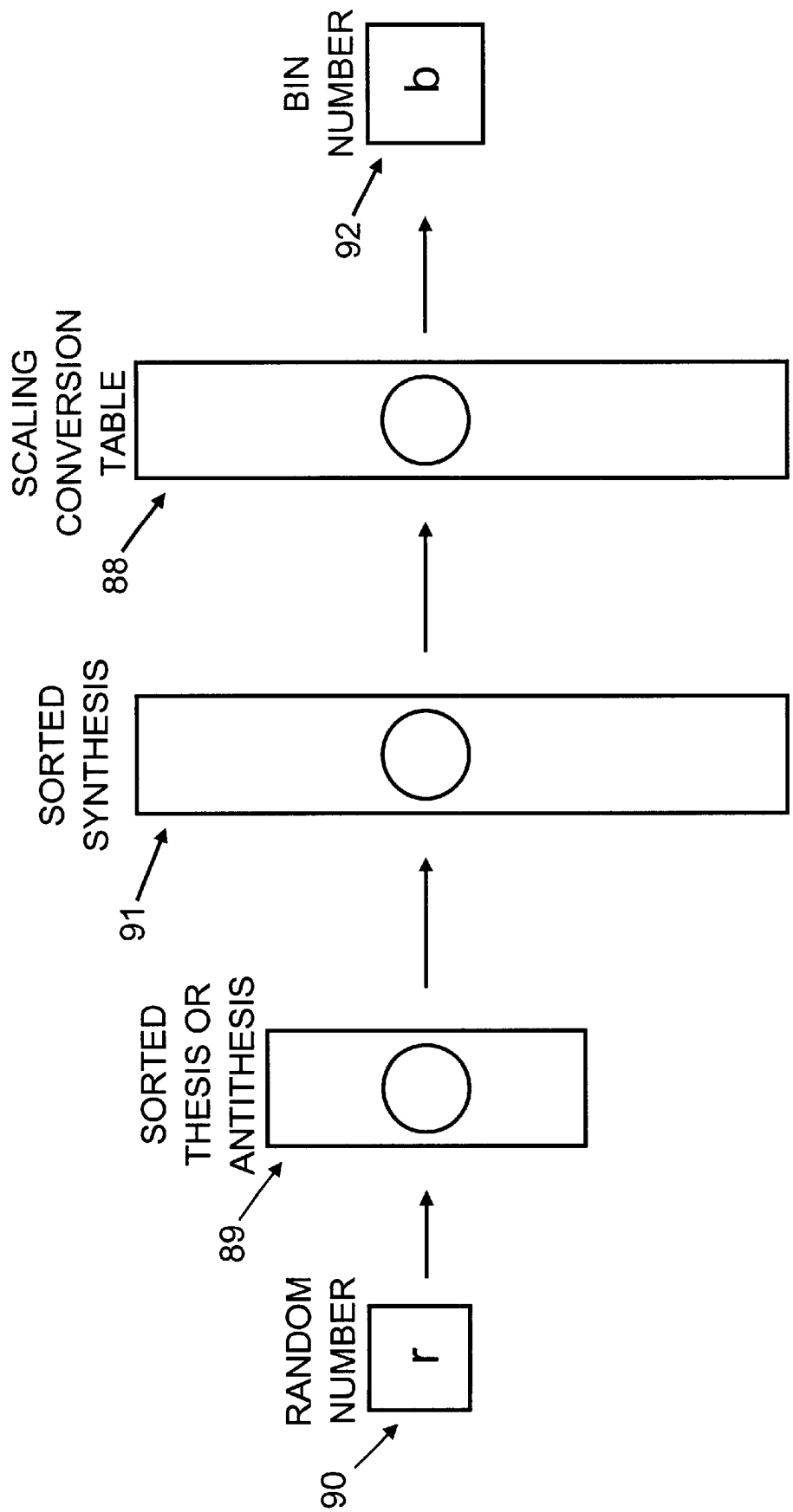
FIG. 16 is a block diagram of a method in accordance with the invention for using the data training sets for training local intelligent agents.

FIG. 16 illustrates the use of the sorted thesis data 84, the sorted antithesis data 85, and the scaling conversion table 88 in producing data to train local intelligent agents. As depicted in the figure, a sample data element is produced from either the sorted thesis population or the sorted antithesis population 89 by first drawing a continuous random number 90r from an interval equal to the total number of samples in the particular data set. This random number 90r is then used to locate and interpolate a data value from the particular data set. Next, the interpolated value is used to locate and interpolate a data value in the sorted synthesis data set 91. Then this latter interpolated data value is used to locate and interpolate a scaled conversion factor in the scaling conversion table 88. Finally, the scaled conversion factor is used to produce a corresponding bin number 92 which is used to advance the corresponding bin count of the local intelligent agent. In the on-line production system, a new data value drawn form the process environment 88 is scaled and "binned" in the manner described.

This method of drawing random samples of data represents virtually an infinite source from which to draw these samples. To avoid possible cyclic behavior of any random number generator, random human intervention is allowed to randomly re-seed the random number generator during the production of data samples.

The neural network-based agents in the library of neural networks are trained in conventional fashion using "acceptable" and simulated "unacceptable" statistical distributions of test results. The end result of this training process is a library of neural network-based agents applicable to different types of test results and varying in the degree of bias error and precision error they can detect.

Figure 17:
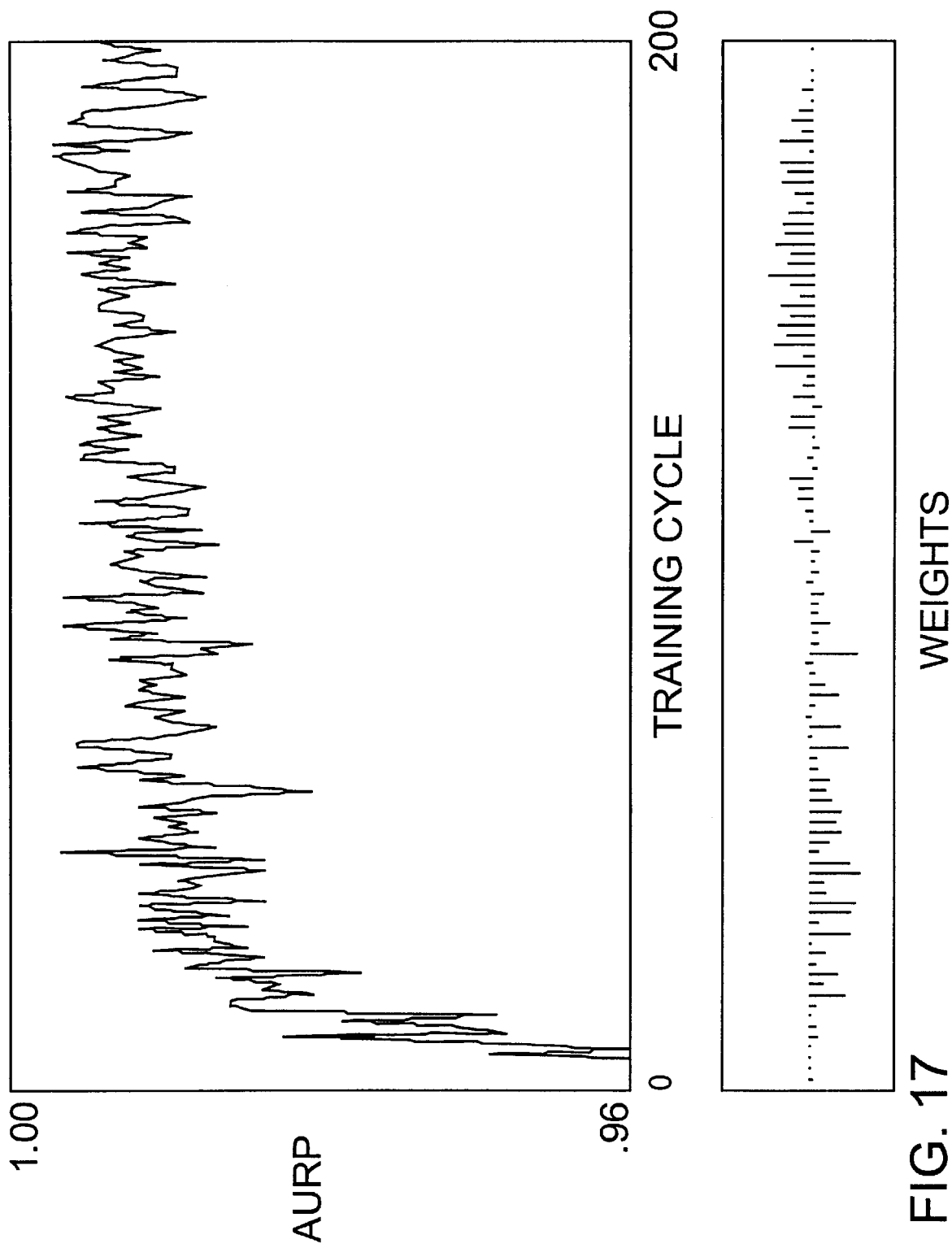
FIG. 17 includes two graphs indicating how the local intelligent agents are trained with the training data sets.

FIG. 17 also relates to local intelligent agent training. In this case a neural network with 101 bins (1 bias bin) has been trained with a 1000 case data set containing 500 negative instances and 500 positive instances. Both positive and negative distributions were derived from normal populations. The means of the two distributions differ by 10% and the variances are equal. This then is an example of bias error. This data was used to draw alternating negative and positive window samples of length 20: 500 positive window clusters and 500 negative window clusters per training cycle. What is seen in the upper portion of the figure are values of the area under the ROC plot (AURP) after each training cycle. After 200 cycles the area converges nicely to a median value of 0.9929. This result has been shown to be far superior to any method that merely analyzes mean values of windowed clusters. Using the last 100 training cycles the following nonparametric confidence intervals for the AURP are realized:

90% confidence interval: 0.9889 to 0.9970

100% confidence interval: 0.9869 to 0.9980

The lower portion of this panel displays the relative weights for each of the 101 bins at the end of training.

The training of Type A local intelligent agents as neural networks may be performed by means of a software simulator as described above that utilizes large error-free data samples drawn from the process environment. In the present embodiment of analyzing patient specimens with a laboratory instrument, 2,000 error-free samples for each of 25 test (analyte) values are first drawn. A software simulator creates a library of trained neural networks for low-bias, high-bias, and precision loss error detection for each of the 25 analytes. The simulator may run in parametric mode or in non-parametric mode. In parametric mode, the collected empirical data is fitted to a normal distribution, or to a skewed normal distribution, or to a skewed normal distribution with kurtosis. In nonparametric mode, the raw data is itself directly sampled during simulation. The simulator can be used to design and train a single neural network for a particular error type with selected error magnitudes and window size, or it can be used to design and train a large library of neural networks for several error types, several error magnitudes and several window sizes. During training, the simulator draws window-sized samples from parametric or nonparametric distributions. For error free data, the samples are taken as drawn. For error-filled data, each error-free data element drawn is offset by the specified bias or precision fraction. All data elements are scaled on the unit interval using the most appropriate scaling method as described above.

D. A Netural Network Embodiment of a Local Intelligent Agent

In a preferred embodiment, Type A local intelligent agents are neural networks that are trained with large samples of error-free values for each of the selected parameters from the process environment. Three neural networks are produced for each parameter: one to detect low bias errors, one to detect high bias errors, and one to detect precision loss errors. The accuracy with which one of these neural networks will detect error is related to three factors: the magnitude of the error to be detected, the number of samples in a time-sequence run (i.e., the window size), and the number of neural network input nodes (i.e., the number of bins). The measure used herein for accuracy in predicting the target errors is the area under the ROC plot (AURP).

Referring again to FIG. 11, the neural network agent 40a is one of a number of such networks in a library, trained in advance to detect bias or precision errors in the processed data elements 28. The library contains neural networks trained to detect different levels of either precision error or bias error in each of the different types of processed data elements that may be encountered. For example, a laboratory chemical analyzer may be utilized to provide 25 different test results from a patient specimen. An installer or operator of a system 18 would then choose neural networks from the library for three error types for each of the 25 types of test results. For each neural network, the operator would also choose a desired level of error detection. These choices result in 75 different selected neural networks each receiving as an input a different stream of processed (scaled and binned) data elements.

Based upon the processed data elements it receives as inputs, neural network agent 40a generates an output 31p indicative of whether an error in the process has occurred. (In the example above with 25 types of test results and three types of errors being monitored, 75 neural networks are producing 75 independent outputs 31p. The output may take the form of an audio, visual, or other signal to the system or system operator. The response to output 31p depends upon the implementation of system 10. In the present embodiment, as will be described, an operator performs an independent evaluation of the operation of the laboratory instrument by having it analyze a control substance and then comparing the test results to the known results. If the control confirms that the instrument is generating erroneous test results, the operator adjusts the instrument as necessary. In other embodiments, the output may be applied directly to the process to adjust its operation. These and other types of feedback that may be implemented are represented by the intervention signals in FIG. 1.

The neural network agent 40a may be a single (FIG. 11a) or multiple (FIG. 11b) layer network trained with the back-propagation learning algorithm or other existing or created paradigms. Many such networks and their training are well known in the art and are described at length in numerous references such as Neural Network Architecture: An Introduction by Judith Dayhoff and Understanding Neural Networks and Fuzzy Logic by S. Kartalopoulos. which are hereby incorporated by reference. The network has a layer of input nodes 31a, 31b etc. which are individually weighted with weights W, to $W_N$. In this invention, each input node represents a predetermined interval of a scaled range of data elements. In the present embodiment, the scaled range is [0,1 ] and the intervals are of equal size such as increments of 0.01 each. The first node 31a corresponds to 0.0–0.01, the second node 31b corresponds to 0.01–0.02. and so forth up to the last node 31n representing the interval 0.99–1.00. Other ranges and intervals, of course, may be used. The inputs to these nodes are the counts of data elements (from the data element set) associated with the nodes. The counts are multiplied by the node weight factor W to produce products that are summed at the output node. The sum R, from the output node is then applied to an activation function that transforms the signal into a bounded output, such as within a range of [0,1]. Typical activation functions are nonlinear functions such as sigmoid, ramp, or hard limiter functioning. The present embodiment uses the sigmoid function to produce output values on the continuous interval 0 (indicating no error in the test results) to 1 (indicating an error in the test results). Output values between 0 and 1 indicate the partial degree of membership with which the window of test results belongs to the error class. In the present embodiment output signals of 0.5 or greater are interpreted as detections of an error.

E. The Use of ROC Methodology

ROC is an acronym for "Receiver Operating Characteristic" which is a descriptive phrase for a prior art computational methodology. Background information on ROC methodology can be found in DeLeo, James M., *"Receiver Operating Characteristic Laboratory (ROCLAB): Software For Developing Decision Strategies That Account For Uncertainty, "IEEE Computer Society,* April 1993" which is hereby incorporated by reference. ROC methodology addresses fundamental issues about how well some test or some intelligent computational process performs in the task of separating two contrasting, dichotomous classes (thesis versus antithesis) of entities such as healthy versus diseased individuals, or error-free versus error-containing data. ROC methodology is uniquely applied here to facilitate and evaluate the training of the local intelligent agents and to enhance the significance of the output signals from these agents.

An important element in ROC methodology is the ROC plot which is a graph of sensitivity (0–1) versus specificity (0–1), or sensitivity versus 1-specificity, for the full range of values of some independent variable x that could be used in a threshold decision rule to classify events into one of the two dichotomous classes A typical decision rule would have a form suggested by the following example:

If $x>x_t$ then "diseased", otherwise 'healthy"

Figure 18:
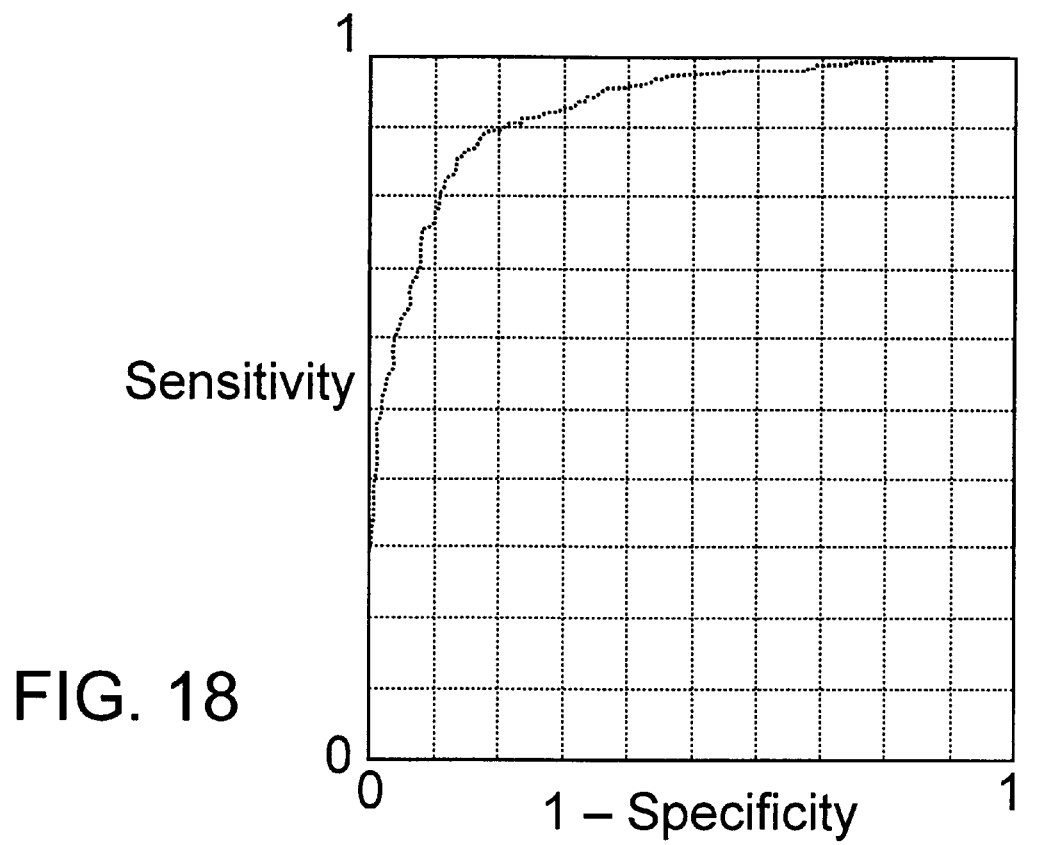
FIG. 18 is an example of a ROC plot in accordance with the invention.

For this to be an appropriate form for a rule, values of x must generally be higher for the diseased cases than for the healthy cases. Given that this is so, it might be asked "What is the best value for $x_t$?" Before this question can be answered, consideration must be given to performance measurements for the rule. The rule can be correct in two ways, first, the rule declares "diseased" and the subject is in fact known to be "diseased", or the rule declares "healthy" and the subject is in fact "healthy." The former is a true positive outcome and the latter is a true negative outcome. When the rule is applied to all events in a data set, the true positive fraction, or sensitivity (the number of events the rule classified as positive that were in fact positive divided by the total number of positive events) and the true negative fraction, or specificity (the number of events the rule classified as negative that were in fact negative divided by the total number of negative events), can be computed for any threshold value $x_t$. When all unique threshold values for x over the entire range of x are evaluated and the resultant sensitivity and specificity values are graphed, a ROC plot is produced as illustrated in the example of FIG. 18. Although ROC plots are usually constructed for the entire range of the independent variable, x, which is $-\infty$ to $+\infty$, they may be constructed for partial ranges of x in certain applications. Every point on the ROC plot corresponds to a particular value for x that could be considered a threshold value $x_t$. Thus, in examining the ROC plot, a prudent choice for $x_t$ can be made by deciding what would be acceptable values for sensitivity and specificity.

In addition to providing a graphical presentation of overall and local performance of an independent variable x in classifying dichotomous classes of events, the ROC plot has several other interesting and useful features. One such feature is that the integral of the ROC plot, or the area under the ROC plot (AURP). This computed value serves as an important measure of how well the independent variable x separates the two classes overall. Another important feature is the derivative or tangent to the ROC plot taken over the entire ROC plot. The range for the magnitude of this tangent is 0 to $\infty$ and the magnitude of the tangent at any point on the ROC plot is exactly the likelihood ratio (lr) that an event having the associated x value will be in the positive class. This likelihood ratio ranges from 0 to $\infty$ and can be converted into a probability that ranges from 0 to 1 by the following formula:

$$p = \frac{lr}{1+lr} \quad (4)$$

Note that when positive and negative outcomes are equally likely, the likelihood ratio is 1 which corresponds to value of 0.5 for p.

In the present embodiment, ROC methodology is used in two ways. A first application of ROC methodology concerns using both the AURP and a "separation index" or "s-index" to monitor and assess the training and validating of classification intelligent agents. A second application concerns improving the response output of local classification intelligent agents by using ROC plot-derived likelihood ratio probability functions as "fuzzy error detection functions" after adjusting them for error prevalence and misclassification costs.

The first application of ROC methodology concerns monitoring and assessing the training and validating of classification intelligent agents. In general, intelligent agents may be used either for classifying events into dichotomous categories such as diseased and healthy individuals, and error-free versus error-containing data, or for constructing mathematical, predictive relationships between input and output values, such as predicting a particular laboratory test value from 24 other test values in the test battery (data frame) associated with a particular specimen. In the present embodiment ROC methodology may be used at the output node of any intelligent agent in which the task of the node is to separate (classify) two distinct, dichotomous classes of events. More specifically, we propose computing the AURP and an s-index after every training cycle to monitor and assess the training of classification intelligent agents, and then later again to assess the performance of the trained intelligent agent when it processes validation data.

During the training of intelligent agents, a measurement such as the root mean square (RMS) is usually calculated and monitored. RMS values range from 0 to 1, where 0 indicates a perfect match between all known and computed outcomes in the training data set and 1 means total divergence between known and computed outcomes for every case. The indication of successful training is that the RMS value becomes successively lower during training and eventually crosses an acceptable preset threshold such as 0.1, indicating successful training and completion of training. Then a similar data set with different data, the validation data set, is processed by the trained agent (e.g., a neural network) and an RMS value is computed. If this RMS value has an acceptable value, the agent has passed training and validation criteria and is now ready for production use. But performance indicators (also known as error functions) and energy functions, like the RMS measure an overall average difference between known outcome and computed outcome for all cases in the data set. In many applications such as in this invention, outcome is dichotomous class (0 or 1) which is either error-free (designated by a 0) or error-containing (designated by a 1). When the classifying intelligent agent is undergoing training, it is given a large number of exemplar data instances representing both error-free and error-containing data. The ideal result of a training session is that the agent would compute 0 for the error-free data in the training set and 1 for the error-containing data. Furthermore, it is also ideal that the validation data set would produce similar results.

As stated earlier, intelligent agents are used in two broad classes of applications, establishing functional relationships between input values and output values, and classification, meaning assigning a class based on input values. Establishing functional relationships means learning a mathematical functional mapping of input values to output values. Neural networks are used in the invention as Type B intelligent agents for this purpose in detecting random errors in a single frame of data. In functional relationship applications, measurements such as RMS are perfectly suitable.

However, for classification applications, another kind of measurement is needed, namely one that evaluates how well the agent is separating the two dichotomous classes of data. For this purpose, the area under the ROC plot (AURP) is used as the measurement of choice. This measurement indicates how well an agent differentiates two dichotomous classes such as, in the present case, error-free and error-containing data. When positive outcome events have generally higher x values than negative outcome events, AURP values range from 0.5 to 1. These AURP values measure how well the values of the independent variable x perform in separating the two classes where 0.5 means no separation and 1 means perfect separation.

Thus one novel use of ROC methodology in the invention is to use it for training classification intelligent agents in general and neural networks in particular by monitoring the AURP during training and using it to evaluate successful training. The intelligent agent output variable x ranges from 0 to 1 and is used as the independent variable for AURP computation.

Next, it is recognized that some intelligent agents will train more perfectly than others. An AURP value of 1 only conveys that x values associated with the positive class events are all higher than all of the x values associated with negative class events and vice versa for an AURP value of 0. Another measurement is needed to convey how well positive and negative events are separated. For this we introduce the notion of a "separation-index" (s-index). An s-index is derived by first computing the difference between two values representing a group measurement for the 0-group and the 1-group of events and then scaling this difference on the 0 to 1 interval. For example, if the mean x values for the two groups were used, the difference of these mean values would be computed first as follows:

$$z = \overline{x_1} - \overline{x_0} \tag{5}$$

In the case where all x values had been previously scaled to the 0–1 interval, computed z values will fall on the −1 to +1 interval. Other values of central tendency such as the median or mode could also be used. An alternative approach that would disambiguate the dichotomous group overlap implied by using central tendency values would be to separately rank order the x values for the negative (0) cases and positive (1) cases and compute a z value that measures the extreme end points of these two distributions as follows:

$$z_1 = {}_1x_{min} - {}_0x_{max} \tag{6}$$

for cases where the positive events have generally higher values than the negative events and $$z_2 = {}_0x_{min} - {}_1x_{max} \tag{7}$$

for cases where the negative events have generally higher values than the positive group. For robustness, both $z_1$ and $z_2$ could be computed and then z could be determined as follows:

$$z = \max(z_1, z_2) \tag{8}$$

Both ways of computing z yield values in the range of −1 to +1. To map these values onto the 0 to 1 s-index interval, the following transformation is used:

$$s-index = \frac{z+1}{2} \tag{9}$$

Just like the AURP, meaningful s-index values from 0.5 to 1 corresponding to increasing quality of separation.

Thus, the first application of ROC methodology in the invention is to use both AURP and the s-index for monitoring and assessing training and for assessing validation for classification intelligent agents such as neural networks.

A second use of ROC methodology has to do with enhancing values of output nodes of classification intelligent agents. These values are real numbers on the 0–1 interval where values closer to 0 suggest membership in the negative class, e.g. error-free data, while those closer to 1 suggest membership in the positive class, e.g. error-containing data. To enhance these output value signals, "fuzzy error detection functions" derived from likelihood ratio values drawn from ROC plots constructed at the end of training and validation are used. These functions treat a neural network node output signal as an independent variable, x (0–1), and map it into a dependent variable value p (0–1), which indicates the probability, or, more generally, the fuzzy possibility that the input event belongs to the error class.

How to obtain these fuzzy functions is next described. When activated by a data set the output node of a well trained classification intelligent agent produces a real number on the 0 to 1 continuous interval. This number could be interpreted as the probability that an error has occurred. Higher numbers correlate with higher probabilities. These output values have corresponding points on the ROC plot associated with the trained agent. The tangent of the ROC plot at these points is the likelihood ratio that the data is in error. These likelihood ratio (lr) values range in magnitude from 0 to ∞ and they can be mapped into a probability (or fuzzy possibility) on the 0–1 interval as follows:

$$p = \frac{lr}{1 + lr} \quad (10)$$

Figure 19:
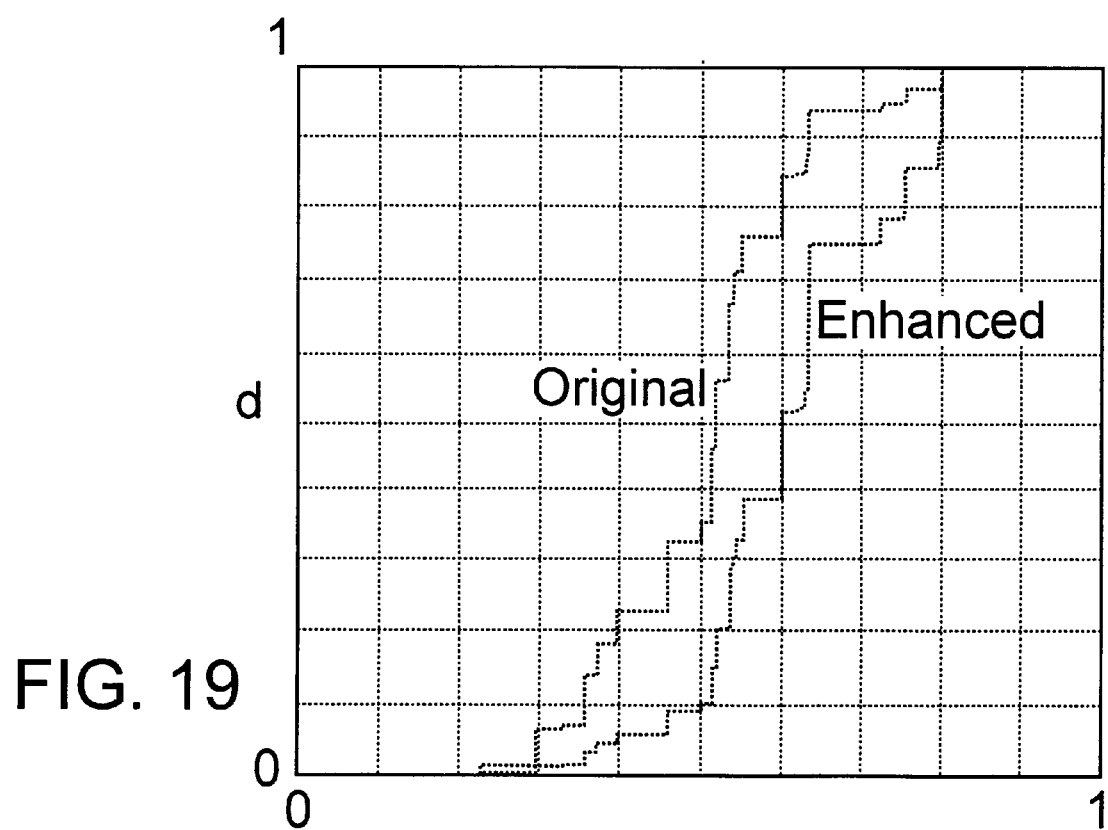
FIG. 19 is an example of a ROC plot derived original and enhanced fuzzy function in accordance with the invention.

When this is done over all values for x, we have an original fuzzy error detection function d versus x as illustrated in FIG. 19. Plots such as these map intelligent agent output values into improved indicators and so we propose that they are used as an essential component of classification intelligent agents.

The perfect ROC plot has only two magnitude values for lr, namely 0 and ∞, which correspond to p values of 0 or 1, respectively. This is because all negative and positive training and/or validation exemplars have been perfectly separated by the intelligent agent. However, in the production environment, it is possible that neural network output values, x, that were not encountered in the training data could appear and that these values could fall between the maximum x value for negative events and the minimum x value for positive events. So, in the case of perfect ROC plots, an unenhanced fuzzy error detection function is constructed as a linear ramp function as suggested by the following equations:

$$0 \leq x \leq {}_0x_{max} \quad p=0 \quad (11)$$

$$_0x_{max} < x < {}_1x_{min} \quad p = \frac{x - {}_1x_{min}}{{}_0x_{max} - {}_1x_{min}} \quad (12)$$

$$_1x_{min} \leq x \leq 1 \quad p=1 \quad (13)$$

Figure 20:
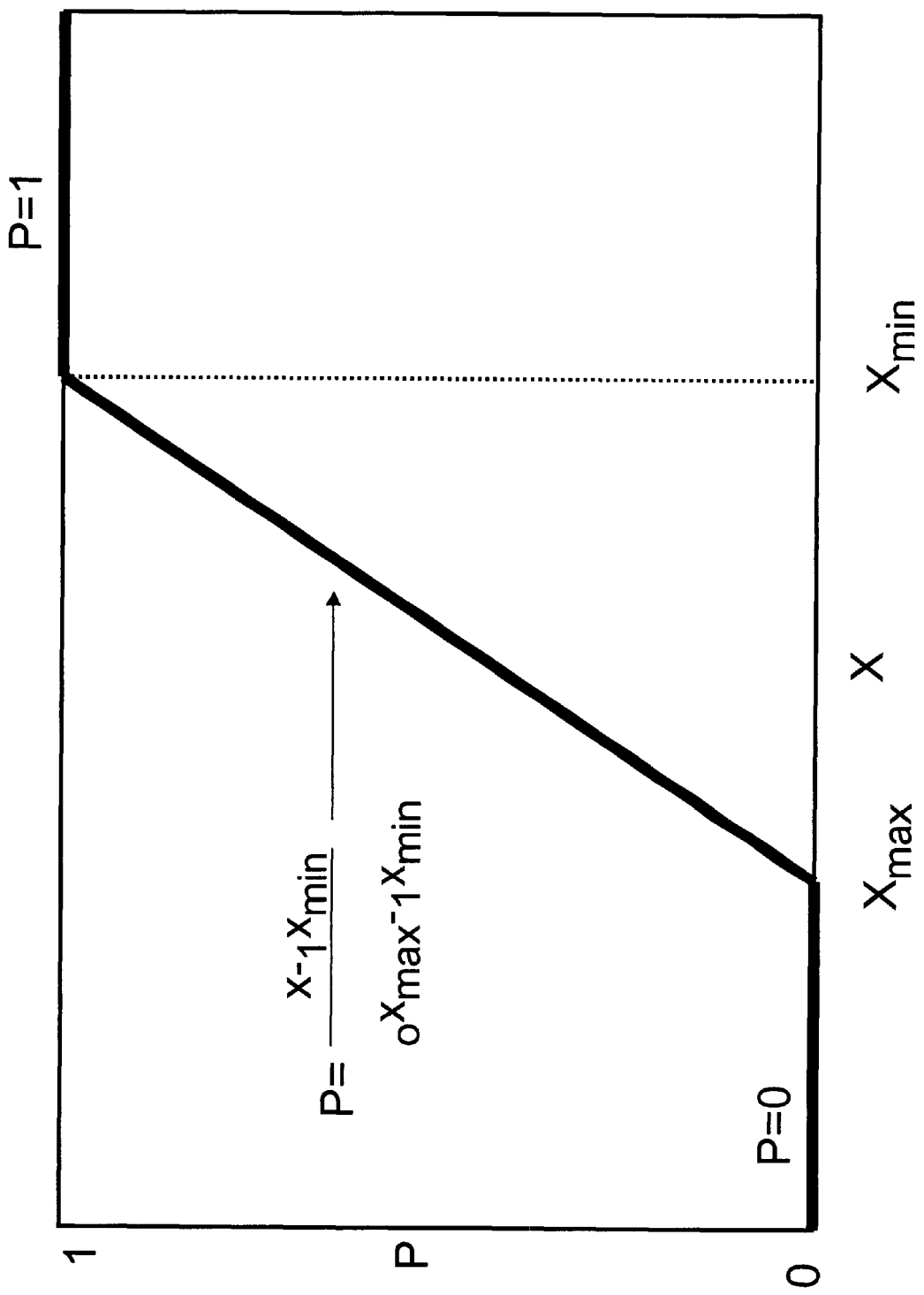
FIG. 20 is an example of an unenhanced fuzzy error detection function for perfect ROC plots.

FIG. 20 illustrates equations 11–13.

Fuzzy functions such as illustrated in FIG. 19 can be improved if expected error prevalence and error misclassification costs are known or can reasonably be estimated. This is accomplished by first finding likelihood ratio values associated with prevalence and then with misclassification costs. The likelihood ratio value associated with prevalence, prev, can be computed as follows:

$$r_{prev} = \frac{prev}{1 - prev} \quad (14)$$

The likelihood ratio value corresponding to misclassification costs, $r_{mc}$, can be expressed in any of the four ways indicated by the following equations:

$$r_{mc} = \frac{FNC}{FPC} \quad (15)$$

$$r_{mc} = \frac{TNB}{TPB} \quad (16)$$

$$r_{mc} = \frac{NTN}{NTP} \quad (17)$$

$$r_{mc} = \frac{NFP}{NFN} \quad (18)$$

in which FNC is tile false negative cost and FPC is the false positive cost; TNB is the true negative benefit and TPB is the true positive benefit; NTN is the number of true negative events that it would take to be in balance with the number of true positive events given by NTP; and NFP is the number of false positive events it should take to balance the number of false negative events given by NFN.

Next the prevalence and misclassification cost likelihood ratio values are combined as a product $$R = r_{prev} r_{mc} \quad (19)$$

and the fuzzy function is converted to an improved fuzzy function by means of the following formula:

$$p_{new} = \frac{R p_{old}}{1 + (R-1) p_{old}} \quad (20)$$

The advantage of using the resulting enhanced fuzzy functions is that they will reflect prevalence and misclassification costs in a balanced way. This means that a p value of 0.5 will correspond to an improved balance threshold cut point that separates negative class data (e.g., error-free data) and positive class (e.g., error containing data). FIG. 19 shows the original fuzzy function associated with the ROC plot shown in FIG. 18. FIG. 19 also shows an "enhanced" fuzzy function which was derived from the above equation using R=0.2 which was computed by assuming a likelihood ratio value, $r_{prev}$=0.1 and a misclassification cost likelihood ratio value, $r_{mc}$=2.

Practical implementation of fuzzy functions and the computational processes to use them can be built into local intelligent agents or indeed, into the central intelligent agent. This involves constructing unenhanced fuzzy functions at the time of training and validation of intelligent agents. Values for $r_{prev}$ and $r_{mc}$ could be set and adjusted in the operational environment. Thus when an intelligent agent produced an output value, this value would be converted through use of the unenhanced fuzzy function and the resulting value would be updated by means of the formula above to produce a $p_{new}$ value from a $p_{old}$ value.

In summary, ROC methodology is used for monitoring the area under the ROC plot (AURP) and a newly introduce s-index value during training of a classification intelligent agent like a neural network, and for constructing fuzzy error detection functions derived from ROC plot derivatives and enhanced with error prevalence and misclassification cost information.

F. Applicability of the Invention

In view of the many possible embodiments to which the principles of the invention apply, it should be recognized that the embodiments described herein are only examples of the invention and not limitations on its scope. For example, the extensions of ROC methodology described herein are not limited to this invention. The scope of the invention, rather, is defined by the following claims. We therefore claim as our invention all that comes within the scope of these claims.

We claim:

1. A computer-implemented method for detecting errors in a process, the method comprising the following steps:
   collecting data elements from the process, the data elements having a range of values;
   counting the number of data elements having values within predetermined intervals of the range;
   applying the counts of data elements as inputs to nodes of a neural network, each count being applied to a node representing the predetermined interval corresponding to the count; and
   generating an output from the neural network based on the inputs, the output indicative of whether an error in the process has occurred.

2. The method of claim 1 wherein the collecting step comprises collecting through a moving window a predetermined number of data elements, and the method includes repeating the above steps after moving the window to replace a data element in the window with another data element outside the window.

3. The method of claim 1 including scaling the data elements to values within a predetermined range before counting the data elements.

4. The method of claim 3 wherein the scaling step comprises scaling the data elements to values within the range of zero to one.

5. The method of claim 1 wherein the process is laboratory analysis of patient specimens, and the collecting step comprises collecting test results from patients, the test results generated by a laboratory instrument from the patient specimens.

6. The method of claim 1 wherein the neural network is trained to detect a bias error or a precision error in the data elements applied as inputs to its nodes.

7. A computer-readable medium on which is stored instructions for executing the steps of claim 1.

8. The method of claim 1 further comprising:
   training the neural network using ROC methodology.

9. The method of claim 8 wherein the neural network is enhanced by incorporating prevalence and misclassification cost information.

10. A computer-implemented method for detecting in real time errors in a process, the method comprising the following steps:
    collecting through a moving window a set of data elements from the process;
    scaling the data elements via a plurality of scaling techniques to generate scaled data elements;
    basing inputs to nodes of a neural network on the scaled data elements;
    generating an output from the neural network based on the inputs, the output indicative of whether an error in the process has occurred; and
    repeating the above steps after moving the window to replace a data element in the window with another data element outside the window.

11. A method for detecting in real time errors caused by a laboratory instrument in the analysis of patient data, the method comprising the following steps:
    collecting through a moving window a number of test results from a number of patients, the test results generated by a laboratory instrument from analysis of patient specimens;
    applying the test results as inputs to nodes of a neural network;
    generating an output from the neural network based on the inputs during operation of the laboratory instrument, the output indicative of whether an error in the analysis of patient specimens has occurred; and
    repeating the above steps after moving the window to replace a test result in the window with another test result outside the window.

12. The method of claim 11 wherein the collecting step comprises collecting through the moving window at least one test result from each of a predetermined number of patients.

13. The method of claim 11 wherein the laboratory analysis generates test results of different types from each patient specimen, and the collecting step includes collecting test results of a same type in corresponding moving windows.

14. The method of claim 11 wherein the applying step comprises:
    counting the number of test results having values within predetermined intervals of a range of values; and
    applying the counts of test results as inputs to the nodes of the neural network, each count being applied to a node representing the predetermined interval corresponding to the count.

15. The method of claim 11 including scaling the test results to values within a predetermined range before counting the test results.

16. A computer system for executing the steps of claim 11.

17. The method of claim 11 further comprising:
    scaling the test results using a plurality of scaling techniques to generate scaled test results;
    wherein the applying comprises applying the scaled test results as inputs to nodes of the neural network.

18. The method of claim 11 further comprising:
    predicting a measured analyte value for a patient from other analyte values for the patent;
    via the predicted measured analyte value, determining whether a spontaneous error has occurred.

19. The method of claim 11 further comprising:
    outputting a degree of membership the window holds for two dichotomous data populations, wherein at least one of the data populations indicates erroneous, unacceptable data.

20. The method of claim 11 further comprising:
    outputting the degree of membership the window holds in a particular error class.

21. A system for detecting errors in the analysis of patient data, comprising:
    a central processing unit;
    a memory device coupled to the central processing unit and including:
        a first data structure for collecting through a moving window a number of test results from a number of patients;
        a second data structure for applying the test results as inputs to nodes of a neural network;
        a neural network for generating an output based on the inputs applied to its nodes, the output indicative of whether an error in the analysis of patient specimens has occurred; and
        a third data structure for moving the window to replace a test result in the window with another test result outside the window,
    the neural network generating additional outputs as the test results in the window change;

wherein the second data structure includes a counter for counting the number of test results having values within predetermined intervals of the range of values and applying the counts of test results as inputs to the nodes of the neural network, each count being applied to a node representing the predetermined interval corresponding to the count.

22. The system of claim 21 including a laboratory instrument for analyzing patient specimens and generating test results therefrom.

23. The system of claim 21 wherein the neural network is trained to detect a bias or precision error in the test results applied as inputs to its nodes.

24. The system of claim 21 wherein the neural network is a multilayer network trained with a back-propagation algorithm.

25. The system of claim 21 wherein the nodes of the neural network correspond to intervals of test result values.

26. The system of claim 21 wherein the second data structure includes means for scaling the test results to values within a predetermined range before counting the test results.

27. A method of detecting, in real-time, errors in data produced by a laboratory instrument in analysis of patient specimens, the method comprising:

collecting through a moving window a plurality of test results from a plurality of patients, the test results generated by the laboratory instrument from the analysis of the patient specimens;

scaling the test results via a plurality of scaling techniques to generate scaled test results;

counting a number of scaled test results occurring in a plurality of ranges to generate counts of the number of scaled test results occurring in the ranges;

applying at least the counts to one or more neural networks of a first type to generate an output indicative of whether a bias or precision error is present; and via one or more neural networks of a second type, predicting a measured analyte value for a patient from other analyte values for the patent to generate an output indicative of whether a spontaneous error is present.

28. A computer-readable medium comprising computer-executable instructions for performing the method of claim 27.

29. A computer-implemented method for detecting, in real time, a spontaneous error in a set of a plurality of measurements of analytes for a patient, the method comprising:

collecting the set of the plurality of measurements of analytes for the patent;

predicting a measured analyte value out of the set from other analyte values in the set; and via the predicted measured analyte value, determining whether a spontaneous error has occurred.

30. The computer-implemented method of claim 29 wherein:

the measurements are taken from a laboratory instrument; and the determining is accomplished during operation of the instrument.

31. A computer-implemented method for detecting, in real time, an error in measurements by an instrument, the method comprising:

applying a window of data representing measurements by the instrument to a neural network, wherein the neural network is trained to output a degree of membership the window holds for two dichotomous data populations; and outputting a degree of membership the window holds for at least one of the data populations, wherein the data population indicates erroneous, unacceptable data.

32. The method of claim 31 wherein the instrument is a laboratory instrument.

33. The method of claim 32 wherein the measurements indicate analyte values for a patient.

\* \* \* \* \*

UNITED STATES PATENT AND TRADEMARK OFFICE
CERTIFICATE OF CORRECTION

PATENT NO. : 6,556,951 B1
DATED : April 29, 2003
INVENTOR(S) : Deleo et al.

It is certified that error appears in the above-identified patent and that said Letters Patent is hereby corrected as shown below:

Column 3,
Line 46, "now chart" should read -- flow chart --.

Column 4,
Line 3, "flowchart" should read -- flow chart --.

Column 5,
Line 8, "Tile computer" should read -- The computer --.
Lines 55-56, "appear are" should read -- appear --.

Column 6,
Line 46, "of a how" should read -- of how --.

Column 7,
Line 55, "with oldest" should read -- with the oldest --.

Column 8,
Line 14, "squashes'" should read -- "squashes" --.

Line 20, "$s = \sum_{l=1}^{10} w_l x_l$" should read -- $s = \sum_{i=1}^{10} w_i x_i$ --.

Lines 43-44, "type computational" should read -- type of computational --.
Line 65, "may used" should read -- may be used --.

Column 9,
Lines 64, "type a" should read -- type A --.

Column 11,
Line 5, "$p'(i) = \frac{R(i)p(i)}{1+[R(i)-1)p(i)]}$" should read -- $p'(i) = \frac{R(i)p(i)}{1+[(R(i)-1)p(i)]}$ --.

Column 12,
Line 48, "[0,1]" should read -- [0,1] --.

Column 14
Line 14, "error free" should read -- error-free --.
Line 56, "outputs 31p." should read -- outputs 31p). --.

UNITED STATES PATENT AND TRADEMARK OFFICE
CERTIFICATE OF CORRECTION

PATENT NO. : 6,556,951 B1
DATED : April 29, 2003
INVENTOR(S) : Deleo et al.

It is certified that error appears in the above-identified patent and that said Letters Patent is hereby corrected as shown below:

Column 15,
Line 10, "Kartalopoulos." should read -- Kartalopoulos, --.
Line 18, "0.01–0.02." should read -- 0.01–0.02, --.
Line 60, "classes" should read -- classes. --.
Line 62, "'healthy'" should read -- "healthy" --.

Column 20,
Line 10, "tile false" should read -- the false --.
Line 33, "error containing" should read -- error-containing --.
Line 52, "introduce" should read -- introduced --.

Column 22,
Line 37, "patent" should read -- patient --.

Column 24,
Line 1, "patent" should read -- patient --.
Line 11, "patent" should read -- patient --.

Signed and Sealed this

Fifth Day of April, 2005

JON W. DUDAS
*Director of the United States Patent and Trademark Office*